US006426229B1

(12) United States Patent
Yamamoto et al.

(10) Patent No.: US 6,426,229 B1
(45) Date of Patent: Jul. 30, 2002

(54) CHELATING AGENT AND DETERGENT COMPRISING THE SAME

(75) Inventors: Hiroshi Yamamoto, Yokohama; Yasuyuki Takayanagi, Matsudo; Kiyobumi Takahashi, Tokyo; Teturo Nakahama, Iwaki, all of (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 0 days.

(21) Appl. No.: 09/754,211

(22) Filed: Jan. 5, 2001

Related U.S. Application Data

(62) Division of application No. 09/352,132, filed on Jul. 13, 1999, which is a continuation of application No. 08/764,510, filed on Dec. 12, 1996, now abandoned.

(30) Foreign Application Priority Data

| | | |
|---|---|---|
| Dec. 22, 1995 | (JP) | 7-349512 |
| Dec. 22, 1995 | (JP) | 7-349513 |
| Dec. 22, 1995 | (JP) | 7-349514 |
| Dec. 28, 1995 | (JP) | 7-352124 |
| Dec. 28, 1995 | (JP) | 7-352125 |
| Dec. 28, 1995 | (JP) | 7-352126 |
| Dec. 28, 1995 | (JP) | 7-352127 |
| Dec. 28, 1995 | (JP) | 7-352128 |
| Dec. 28, 1995 | (JP) | 7-352129 |
| Jan. 17, 1996 | (JP) | 8-022999 |
| Jan. 22, 1996 | (JP) | 8-026215 |
| Feb. 2, 1996 | (JP) | 8-039075 |
| Feb. 2, 1996 | (JP) | 8-039076 |
| Feb. 2, 1996 | (JP) | 8-039077 |
| Apr. 18, 1996 | (JP) | 8-119502 |

(51) Int. Cl.[7] .......... C11D 3/32; G01N 33/20
(52) U.S. Cl. .......... 436/90; 510/480
(58) Field of Search .......... 436/90; 510/480

(56) References Cited

U.S. PATENT DOCUMENTS

| | | | | | |
|---|---|---|---|---|---|
| 3,637,511 | A | * | 1/1972 | Yang | 252/527 |
| 3,697,453 | A | | 10/1972 | Tate et al. | |
| 3,717,591 | A | * | 2/1973 | Yang | 252/545 |
| 3,991,000 | A | | 11/1976 | Chazard et al. | |
| 4,668,420 | A | * | 5/1987 | Diehl et al. | 252/135 |
| 4,704,233 | A | * | 11/1987 | Hartman et al. | 252/527 |
| 4,973,730 | A | * | 11/1990 | Baur et al. | 558/372 |
| 5,362,412 | A | | 11/1994 | Hartman et al. | |
| 5,466,867 | A | * | 11/1995 | Lin et al. | 562/554 |
| 5,543,566 | A | | 8/1996 | Takahashi et al. | |
| 5,554,791 | A | * | 9/1996 | Lin et al. | 562/565 |
| 5,587,512 | A | * | 12/1996 | Lin et al. | 562/565 |
| 5,707,836 | A | * | 1/1998 | Endo et al. | 435/109 |
| 5,786,313 | A | * | 7/1998 | Schneider et al. | 510/219 |

FOREIGN PATENT DOCUMENTS

| | | | |
|---|---|---|---|
| DE | 2220 295 | | 11/1972 |
| DE | 3833047 | * | 4/1990 |
| DE | 4240695 | * | 6/1994 |
| DE | 4240697 | * | 6/1994 |
| DE | 42 40 697 A1 | | 6/1994 |
| EP | 0 030 461 | | 6/1981 |
| EP | 0 089 136 | | 9/1983 |
| EP | 0 287 846 | | 10/1988 |
| EP | 317542 | | 5/1989 |
| EP | 0 509 382 | | 10/1992 |
| EP | 513948 | | 11/1992 |
| EP | 0 584 665 A2 | | 3/1994 |
| GB | 1 439 518 | | 6/1976 |
| GB | 1439518 | * | 6/1976 |
| JP | 56-44119 | | 10/1981 |
| JP | 57-61799 | | 12/1982 |
| WO | 94/03572 | | 2/1994 |
| WO | 94/20599 | | 9/1994 |
| WO | WO 94/29421 | * | 12/1994 |
| WO | WO 95/12570 | * | 5/1995 |
| WO | WO95/12570 | | 5/1995 |

OTHER PUBLICATIONS

1 ES–A–443127 (Chemical Abstract) Investigation, Procedimientos y Marcas S.A. (Inpromsa), Spain, Nov. 1975.

Chemical Abstract, vol. 123, No., Jul. 17, 1995, Columbus, Ohio, US: abstract No. 33647, XP002063745 & JP 07 089 913 A (Nitto Chemical Industry Co Ltd).

Chemical Abstracts, vol. 95, No. 2, Jul. 13, 1981, Columbus, Ohio, US; abstract No. 9124, XP002063746 & JP 55 160 099 A (Kureha Chemical Industry Co Ltd).

Chemical Abstracts, vol. 63, No. 13, Columbus, Ohio, US; abstract No. 17982f, XP002063747 *abstract* & IT 652 720 A (A.R. Egli).

* cited by examiner

*Primary Examiner*—John Hardee
(74) *Attorney, Agent, or Firm*—Manelli Denison & Selter PLLC; Paul E. White, Jr.

(57) ABSTRACT

The present invention relates to a biodegradable aminocarboxylic acid chelating agent excellent in biodegradability and for use as a chelating agent, which is in the form of a solid, aqueous solution or slurry excellent in handling ability, wherein the chelating agent comprises a detergent composition having excellent detergency and high biodegradability.

5 Claims, No Drawings

CHELATING AGENT AND DETERGENT COMPRISING THE SAME

This is a continuation of application Ser. No. 09/352,132, filed Jul. 13, 1999 now allowed, which is a continuation of application Ser. No. 08/764,510, filed Dec. 12, 1996 now abandoned.

BACKGROUND OF THE INVENTION (1) Field of the Invention

The present invention relates to an amino-carboxylic acid chelating agent excellent in biodegradability and to the uses of the chelating agent. More particularly, it relates to a biodegradable chelating agent in the form of solid, aqueous-solution or slurry excellent in handleability and a detergent composition having excellent detergency and high in biodegradability which comprises the biodegradable chelating agent.

(2) Description of the Related Art

In general, chelating agents used in the form of solid are stored in the form of powder or flake in a bag or a hopper. Solid chelating agents gradually change to a hard mass due to the hardening property depending on accumulation condition and period and preservation condition and period. Therefore, the mass must be crushed just before the use and this is very inconvenient in handling.

Chelating agents used as aqueous solution or slurry are not needed to crush, but have serious problems such as deterioration in purity owing to decomposition in aqueous solution and coloration.

Generally, aminocarboxylic acid chelating agents are widely used as components of photographic bleaching agents, detergent compositions, detergent builders, heavy metal sequestering agents, stabilizers for peroxides and the like.

The detergent compositions are widely used for household cleaning of kitchenware, household cleaning of clothing, cleaning of dinnerware for business purpose, cleaning of plant, cleaning of clothing for business purpose, and the like. Furthermore, they are used as bleaching agents, descaling agents, metal sequestering agents, and the like together with additives suitable for the use.

Sodium tripolyphosphate which has hitherto been used as detergent builders is high in chelating performance. However, it contains phosphorus and causes eutrophication of rivers and lakes when it is discharged into environment. Thus, it is no longer used at present.

Zeolites which are used as detergent builders at present have disadvantages that they are low in chelating performance and have no biodegradability because they are inorganic materials. Furthermore, zeolites are insoluble in water and have a restriction in that they cannot be used for liquid detergents, especially clear liquid detergents. Moreover, zeolites have many problems such that they stick to inner wall of drainage pipes or settle at the bottom of rivers to cause formation of sludges. Therefore, the attempt is being made to reduce the amount of zeolites used and substitutes for zeolites which have sufficient chelating power and detergency have been desired, but such substitutes have not yet been obtained.

Of the aminocarboxylic acids which have been used as detergent builders, ethylenediaminetetraacetic acid (EDTA) has an excellent chelating power in a wide pH range, but is poor in biodegradability and is difficult to degrade by the usual waste water treatments which employ activated sludges. Furthermore, nitrilotriacetic acid (NTA) has a certain biodegradability, but is not preferred from the point of environmental health because it has been reported that NTA has teratogenicity and nitrilotriacetic acid-iron complex has carcinogenicity. Among other conventional aminocarboxylic acids, those which are excellent in chelating performance, but are low in biodegradability have the difficulty that they accumulate as injurious heavy metals in the environment when they are discharged into the environment. Various compounds have been studied as for the above-mentioned organic amino acids, but those which are excellent in chelating performance and biodegradability have not yet been reported at present.

SUMMARY OF THE INVENTION

The object of the present invention is to provide a biodegradable powdery chelating agent which does not harden into a mass during storage or a biodegradable chelating agent in the form of aqueous solution or slurry which does not undergo decomposition or discoloration during storage and to further provide a detergent composition comprising the chelating agent.

As a result of intensive research conducted by the inventors in an attempt to solve the above problems, it has been found that some chelating agents even in the form of solid can be handled easily without becoming hard under a specific condition, some chelating agents even in the form of aqueous solution or slurry can be handled stably and easily over a long period of time without undergoing decomposition or discoloration under a specific condition, and, further, a high detergency can be obtained by combining these biodegradable chelating agents with surface active agents and the like. Thus, the present invention has been accomplished.

That is, the chelating agent of the present invention is a chelating agent which comprises a compound of the following formula [1] and at least one compound selected from the group consisting of aspartic acid, maleic acid, acrylic acid, malic acid, glycine, glycolic acid, iminodiacetic acid, nitrilotriacetic acid, α-alanine, β-alanine, iminodipropionic acid, fumaric acid, an amino acid as a starting material for synthesis of the compound of the formula [1] (hereinafter referred to as "synthetic starting amino acid"), an intermediate amino acid produced in the synthesis reaction of the compound of the formula [1] (hereinafter referred to as "synthetic intermediate amino acid"), and salts thereof in an amount of 25% by weight or less based on the compound of the formula [1] and in the form of aqueous solution or slurry, or in an amount of 8% by weight or less based on the compound of the formula [1]:

[1]

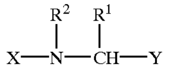

wherein $R^1$ represents hydrogen or an unsubstituted or substituted hydrocarbon group of 1–10 carbon atoms and $R^2$ represents hydrogen or an unsubstituted or substituted hydrocarbon group of 1–8 carbon atoms, with a proviso that $R^1$ and $R^2$ may form a ring together, the substituent which can be present in $R^1$ and $R^2$ is at least one member selected from the group consisting of —OH, —$CO_2M$ and —$SO_3M$ where M represents hydrogen or an alkali metal; X represents

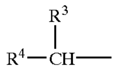

or

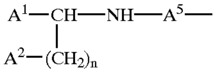

where $R^3$ represents hydrogen or an unsubstituted or substituted hydrocarbon group of 1–8 carbon atoms, the substituent is at least one member selected from the group consisting of —OH, —$CO_2M$ and —$SO_3M$, $R^4$ represents at least one member selected from the group consisting of hydrogen, —$CO_2M$ and —$SO_3M$, $A^1$ and $A^2$ each represent one member selected from the group consisting of hydrogen, $CO_2M$ and $SO_3M$, $A^5$ represents an alkylene group of 1–8 carbon atoms which may be of straight chain or branched chain or may form a ring, the alkylene group may contain in the chain an ether bond —O—, an ester bond —COO— or an amide bond —CONH—, M represents hydrogen or an alkali metal, and n represents an integer of 1–8; and Y represents at least one member selected from the group consisting of hydrogen, $CO_2M$ and $SO_3M$.

Furthermore, the chelating agent of the present invention is a chelating agent in the form of aqueous solution or slurry which comprises a compound of the above formula [1] and at least one compound selected from the group consisting of aspartic acid, maleic acid, acrylic acid, malic acid, glycine, glycolic acid, iminodiacetic acid, nitrilotriacetic acid, α-alanine, β-alanine, iminodipropionic acid, fumaric acid, a synthetic starting amino acid, a synthetic intermediate amino acid, and salts thereof in an amount of 25% by weight or less based on the compound of the formula [1].

Moreover, the present invention relates to detergent compositions having excellent detergency and comprising the said biodegradable chelating agents.

PREFERRED EMBODIMENTS OF THE INVENTION

As the monoamine compounds of the formula [1] where X is

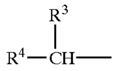

(wherein $R^3$ and $R^4$ are as defined above), mention may be made of, for example, aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)aspartic acid (SMAS), N-(2-sulfoethyl)aspartic acid (SEAS), glutamic acid-N,N-diacetic acid (GLDA), N-(2-sulfomethyl)glutamic acid (SMGL), N-(2-sulfoethyl)glutamic acid (SEGL), N-methyliminodiacetic acid (MIDA), α-alanine-N,N-diacetic acid (α-ALDA), β-alanine-N,N-diacetic acid (β-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA) and alkali metal salts or ammonium salts thereof.

These compounds have asymmetric carbon and, hence, exist as optical isomers. From the viewpoint of biodegradability, preferred are (S)-aspartic acid-monoacetic acid, (S)-aspartic acid-N,N-diacetic acid, (S)-aspartic acid-monopropionic acid, (S,S)-iminodisuccinic acid, (S,R)-iminodisuccinic acid, (S)-2-sulfomethylaspartic acid, (S)-2-sulfoethylaspartic acid, (S)-glutamic acid-N,N-diacetic acid, (S)-2-sulfomethylglutamic acid, (S)-2-sulfoethylglutamic acid, (S)-α-alanine-N,N-diacetic acid, (S)-serine-N,N-diacetic acid, and (S)-phenylalanine-N,N-diacetic acid and alkali metal salts or ammonium salts thereof.

As the diamine compounds represented by the formula [1] where X is

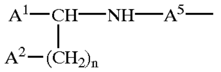

(where $A^1$, $A^2$ and $A^5$ are as defined above), mention may be made of, for example, ethylenediaminedisuccinic acid (EDDS), 1,3-propanediaminedisuccinic acid (13PDDS), ethylenediaminediglutaric acid (EDDG), 1,3-propanediaminediglutaric acid (13EDDG), 2-hydroxy-1,3-propanediaminedisuccinic acid (PDDS-OH) and 2-hydroxy-1,3-propanediaminediglutaric acid (PDDG-OH) and alkali metal salts or ammonium salts thereof.

These compounds have asymmetric carbon and, hence, there exist optical isomers. From the viewpoint of biodegradability, preferred are (S,S)-ethylenediaminedisuccinic acid, (S,S)-1,3-propanediaminedisuccinic acid, (S,S)-ethylenediaminediglutaric acid, (S,S)-1,3-propanediaminediglutaric acid, (S,S)-2-hydroxy-1,3-propanediaminedisuccinic acid and (S,S)-2-hydroxy-1,3-propanediaminediglutaric acid and alkali metal salts or ammonium salts thereof.

The monoamine compounds are generally obtained by a process which comprises subjecting the starting amino acid or sulfonic acid to addition reaction with hydrocyanic acid and formalin and hydrolyzing the resulting addition product under alkaline condition or a process which comprises subjecting amino acid or sulfonic acid to addition reaction with acrylonitrile or the like and hydrolyzing the resulting addition product under alkaline condition. Therefore, the desired monoamine chelating agents usually contain side reaction products as impurities in addition to the starting amino acid or sulfonic acid.

For example, in the synthesis of taurine-N,N-diacetic acid salt by adding hydrocyanic acid and formalin to taurine and, then, hydrolyzing the resulting addition reaction product, there are formed by-products such as glycolic acid, glycine, iminodiacetic acid, nitrilotriacetic acid, fumaric acid, β-alanine and iminodipropionic acid in addition to unreacted taurine. In addition to these impurities, impurities such as malic acid and acrylic acid salts are sometimes detected depending on reaction conditions.

The diamine compounds are generally-produced by adding two molecules of maleic acid to one molecule of an alkylenediamine. In this case, the resulting desired diamine chelating agents usually contain, as impurities, unreacted maleic acid, reaction intermediate amino acid having only one molecule of maleic acid added and side reaction products thereof. For example, in the synthesis of an ethylenediaminedissucinic acid salt by adding two molecules of maleic acid to one molecule of ethylenediamine, there are seen by-products such as ethylenediaminemonosuccinic acid, fumaric acid and malic acid in addition to unreacted maleic acid.

Furthermore, for the production of the diamine compounds, there is a process according to which two molecules of the starting amino acid such as aspartic acid or glutamic acid are linked using dihaloethane, epichlorohydrin or the like. In this case, the resulting desired diaminopolycarboxylic acid chelating agents usually contain, as impurities, the starting amino acid, a reaction intermediate amino acid having only one molecule of the starting amino acid added and side reaction products thereof. For example, in the synthesis of (S,S)-ethylenediaminedissucinic acid by adding two molecules of (S)-aspartic acid to one molecule of dichloroethane and, then, subjecting the addition reaction product to precipitation with addition of a mineral acid, there are seen by-products such as (S)-N-2-chloroethylaspartic acid, (S)-N-2-hydroxyethylaspartic acid, (S,S)-N-2-hydroxyethylethylenediaminedisuccinic acid and fumaric acid in addition to unreacted (S)-aspartic acid.

In the present invention, the chelating agent is prepared so that the content of the above-mentioned impurity salts is 25% by weight or less, preferably 8% by weight or less based on the weight of the compound of the formula [1] in the form of a salt. When such condition is satisfied, especially when the content of the impurity salts is 8% by weight or less, the hardening of the resulting chelating agent is considerably inhibited even in the ordinary storing state. The total amount of the impurity salts is more preferably 3% by weight or less based on the weight of the compound of the formula [1], and further preferably 0.5% by weight or less for considerably inhibiting the hardening into a mass even under the severer storing conditions. When these conditions are satisfied, a powder inhibited from hardening into a mass can be obtained only by concentrating the reaction mixture for synthesis of the compound of the formula [1] (hereinafter referred to as merely “reaction mixtures”) and, thereafter, subjecting the concentrated reaction mixture to spray drying and the like, but, in other cases, amount of the impurity salt can be reduced by carrying out the following purification.

As the surest purification means for the chelating agent, there is a method which comprises once subjecting the reaction mixture to precipitation with addition of a mineral acid such as sulfuric acid to isolate the chelating agent as a crystal of high purity and, then, redissolving the crystal in alkaline water. Further, when a solid crude chelating agent is purified, it is also effective to wash the chelating agent with an alcohol such as methanol to remove low-molecular impurities high in solubility.

In the present invention, when the impurities are in the form of acids, the chelating agents are also prepared in the same manner as in the case of the impurities being in the form of salts, namely, so that the content of these impurity acids is 25% by weight or less, preferably 8% by weight or less based on the compound of the formula [1]. When such condition is satisfied, especially when the content of the impurity acids is 8% by weight or less, the hardening of the resulting chelating agent is considerably inhibited even in the ordinary storing state. The total amount of the impurity acids is more preferably 3% by weight or less based on the compound of the formula [1], and further preferably 0.5% by weight or less for considerably inhibiting the hardening even under the severer storing conditions.

If the total content of the impurity acids (salts) cannot be permitted to meet with the above conditions by subjecting the chelating agent obtained by the above-mentioned reaction to only one precipitation operation with addition of an acid, the crude crystal may be purified by washing it with a large amount of water, by repeating recrystallization of the crude crystal, or by other methods.

The chelating agent purified to 25% by weight or less in the content of impurities by these methods can be easily returned to a powdery or flaky form even if the chelating agent sets during being stored or transported in the form of crystal or flake. Thus, the chelating agent can be stably and easily handled over a long period of time.

In the present invention, the chelating agent adjusted to contain the impurity salts in an amount of 25% by weight or less, preferably 10% by weight or less, more preferably 5% by weight or less based on the compound of the formula [1] can also be used in the form of an aqueous solution or slurry. When the chelating agent obtained by the above-mentioned reaction satisfies the above condition, the reaction mixture can be used as it is, but if the content of impurities exceeds the above range, an additional operation is needed for purification.

The chelating agent purified to 25% by weight or less in terms of the content of impurity salts by the above methods can be used as an aqueous solution or slurry containing at least 10% by weight of water, but from the points of preservativity and handleability, desirably, it is used as an aqueous solution or slurry of 5–80% by weight, preferably 20–50% in the salt concentration of chelating agent.

The materials of drums, tank lorries, storage tanks, stirrers and the like used for handling such as storing, transportation or mixing may be any of alloys, glass linings, synthetic resin linings and the like, and stainless steel is especially preferred.

The temperature at which the chelating agent of the present invention is handled is preferably 0–75° C. in the case of the compound concentration being 5–40% by weight, 5–75° C. in the case of the compound concentration being 40–50% by weight, and 10–75° C. in the case of the compound concentration being 50–80% by weight.

Ordinarily, storage for about 3 years is possible under these conditions, and an aqueous solution or slurry of chelating agent not deteriorated in quality can be easily taken out and used as required.

The chelating agents obtained in this way constitute detergents having excellent detergency with addition of surface active agents and other additives.

These chelating agents are used normally in the form of alkali metal salts such as sodium salt and potassium salt, but can be used in the form of partially neutralized aqueous solution obtained by dissolving an acid form crystal isolated by precipitation with addition of an acid in an alkaline aqueous solution, in the form of the reaction mixture which is an alkaline aqueous solution, in the form of a solid salt obtained by concentrating the above aqueous solution, or in any other forms. If necessary, these can be adjusted to a pH suitable for the use. That is, the chelating agents of the present invention can be used in any forms of powder or flake inhibited from hardening into a mass and aqueous solution or slurry.

Next, the detergent composition of the present invention will be explained.

The detergent composition of the present invention contains the chelating agent of the present invention, especially, (S)-aspartic acid-N,N-diacetic acid, N-methyliminodiacetic acid and/or taurine-N,N-diacetic acid and, if necessary, a nonionic surface active agent, an anionic surface active agent, a silicate, a bleaching agent and/or a fatty acid salt.

The nonionic surface active agents usable in the present invention include, for example, ethoxylated nonylphenols, ethoxylated octylphenols, ethoxylated sorbitan fatty acid esters and propylene oxide adducts thereof, and are not especially limited. However, compounds obtained by random or block addition of 5–12, preferably 6–8 on an average of ethylene oxides and 0–12, preferably 2–5 on an average of propylene oxides per one molecule of an alcohol or phenol represented by the following formula [2], for example, ethoxylated primary aliphatic alcohols, ethoxylated secondary aliphatic alcohols and propylene oxide adducts thereof have especially high detergency. These nonionic surface active agents can be used each alone or in admixture of two or more.

R—OH [2]

(R: an alkyl, alkenyl or alkylphenyl group of 8–24 carbon atoms).

The anionic surface active agents usable in the present invention include, for example, straight chain alkylbenzenesulfonic acid salts having alkyl group of 8–16 carbon atoms on an average, a-olefin sulfonic acid salts of 10–20 carbon atoms on an average, aliphatic lower alkyl sulfonic acid salts or salts of aliphatic sulfonation products which are represented by the following formula [3], alkylsulfuric acid salts of 10–20 carbon atoms on an average, alkyl ether sulfuric acid salts or alkenyl ether sulfuric acid salts having a straight chain or branched chain alkyl or alkenyl group of 10–20 carbon atoms on an average and having 0.5–8 mols on an average of ethylene oxide added thereto, and saturated or unsaturated fatty acid salts of 10–22 carbon atoms on an average.

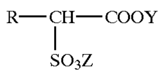

[3]

(R: an alkyl or alkenyl group of 8–20 carbon atoms, Y: an alkyl group of 1–3 carbon atoms or a counter ion, and Z: a counter ion).

The silicates usable in the present invention are silicates represented by the following formula [4] or aluminosilicates represented by the following formula [5], and these can be used each alone or in admixture of two or more at an optional ratio. Amount of the silicates is 0.5–80% by weight, preferably 5–40% by weight in the detergent compositions.

$LM'Si_xO_{2(x+1)}.yH_2O$ [4]

(L represents an alkali metal, M' represents sodium or hydrogen, x represents a number of 1.9–4, and y represents a number of 0–20).

$Na_z[(AlO_2)_z(SiO_2)_y].H_2O$ [5]

(z represents a number of 6 or more, y represent a number which satisfies the ratio of z and y being 1.0–0.5, and x represents a number of 5–276).

The bleaching agents usable in the present invention include, for example, sodium percarbonate and sodium perborate. The amount of these bleaching agents is 0.5–60% by weight, preferably 1–40% by weight, more preferably 2–25% by weight in the detergent composition.

The fatty acid salts used in the present invention include, for example, alkali metal salts, alkaline earth metal salts, ammonium salts or unsubstituted or substituted amine salts, preferably alkali metal salts or alkaline earth metal salts, more preferably alkali metal salts of saturated or unsaturated fatty acids of 10–24 carbon atoms on an average. These fatty acid salts may also be used in admixture of two or more.

Examples of the fatty acid salts used in the present invention are alkali metal salts, alkaline earth metal salts, ammonium salts or unsubstituted or substituted amine salts, preferably alkali metal salts, alkaline earth metal salts, ammonium salts or unsubstituted or substituted amine salts, more preferably alkali metal salts of lauric acid, myristic acid, stearic acid and the like.

The detergent compositions of the present invention may further contain various additives such as stabilizers, alkali salts, enzymes, perfumes, surface active agents other than those of nonionic and anionic types, scale inhibitors, foaming agents and anti-foaming agents.

Detergent compositions of further higher performance can be obtained by using a plurality of the chelating agents in combination.

In some cases, chelating power cannot be sufficiently exhibited with use of one chelating agent depending on the pH employed, but excellent detergent compositions having detergency which is not influenced by the change of pH in the environment where they are used can be obtained by using a plurality of the chelating agents in admixture.

The chelating agents used in the detergent compositions of the present invention which are excellent in adaptability to pH are three of (S)-aspartic acid-N,N-diacetic acid, taurine-N,N-diacetic acid and N-methyliminodiacetic acid. Features of each of them will be explained below.

(S)-aspartic acid-N,N-diacetic acid can be used in the detergent compositions of the present invention excellent in adaptability to pH. Particularly, it imparts excellent performance in the neutral pH region, and, therefore, is preferred. It is especially great in chelate stability constant for calcium or the like among the above-mentioned three N,N-diacetic acid type chelating agents. Therefore, also in combination with carboxylic acid surface active agents such as sodium laurate, (S)-aspartic acid-N,N-diacetic acid chelates the objective metals firmly and is preferred.

It has been reported that the chelate stability constant for calcium of nitrilotriacetic acid is 6.4 and that of (S)-aspartic acid-N,N-diacetic acid is 5.8. However, there is a fact that as for the actual builder performance, (S)-aspartic acid-N,N-diacetic acid is superior to nitrilotriacetic acid. Since (S)-aspartic acid-N,N-diacetic acid is a monoamine chelating agent having four carboxyl groups, it can trap the objective metals such as calcium by quinquedentate coordination at the maximum. Therefore, when compared with nitrilotriacetic acid having three carboxyl groups and trapping the objective metals such as calcium by quadridentate coordination at the maximum, the chelating power of (S)-aspartic acid-N,N-diacetic acid is higher than that of nitrilotriacetic acid and exhibits conspicuously superior performance in the neutral region.

In combination with a sulfonic acid surface active agent such as sodium dodecylbenzenesulfonate, (S)-aspartic acid-N,N-diacetic acid has a $Ca^{++}$ trapping power which is higher than that of nitrilotriacetic acid at a pH of 7–8 and equivalent to that of ethylenediaminetetraacetic acid.

When sodium laurate which is a carboxylic acid surface active agent is used in place of sodium dodecylbenzenesulfonate which is a sulfonic acid surface active agent, (S)-aspartic acid-N,N-diacetic acid retains a $Ca^{++}$ trapping power of about 50% at a pH of 12. The $Ca^{++}$ trapping power of (S)-aspartic acid-N,N-diacetic acid is inferior to that of ethylenediaminetetraacetic acid which retains a $Ca^{++}$ trapping power of about 90% with the same substitution of the surface active agent as above, but is surprising in view of the fact that most of the known monoamine chelating agents completely lose the $Ca^{++}$ trapping power in the presence of carboxylic acid surface active agents.

(S)-aspartic acid-N,N-diacetic acid is completely decomposed to inorganic materials in biodegradability tests such as 302A Modified SCAS Test described in OECD Guideline for Testing of Chemicals. It is completely decomposed in a certain period of time by activated sludges domesticated with waste water containing (S)-aspartic acid-N,N-diacetic acid.

Taurine-N,N-diacetic acid can be used in the detergent compositions of the present invention excellent in adaptability to pH and is especially preferred since it imparts an excellent performance in the weakly alkaline pH region.

As the chelate stability constant for calcium, a value of 4.2 has been reported for taurine-N,N-diacetic acid. However, on actual builder performance, there is a fact that taurine-N,N-diacetic acid is superior to nitrilotriacetic acid. When molecular structure of taurine-N,N-diacetic acid is viewed from the point of chelating performance, it comprises iminodiacetic acid portion which directly participates in trapping of the objective metal and sulfonic acid portion which participates in adaptation to pH of the objective metal trapping power. That is, it is considered that the sulfonic acid group of taurine-N,N-diacetic acid does not directly participate in trapping of the objective metal, but arranges the chemical environment so that molecules can readily exhibit the chelating power in more neutral side by the actions such as shifting of isoelectric point to the neutral side.

In combination with sulfonic acid surface active agents, taurine-N,N-diacetic acid has a $Ca^{++}$ trapping power equal to that of ethylenediaminetetraacetic acid at a pH of 8 and superior to that of ethylenediaminetetraacetic acid at a pH of 8.5 or higher. This fact is surprising when compared with the fact that nitrilotriacetic acid which is a typical one of the same N,N-diacetic acid chelating agents exceeds ethylenediaminetetraacetic acid in $Ca^{++}$ trapping power only when pH reaches 10, under the same conditions.

Taurine-N,N-diacetic acid is completely decomposed to inorganic materials in a short time in biodegradability tests such as 302A Modified SCAS Test mentioned above. It is completely decomposed in a short time by activated sludges domesticated with waste water containing tuarine-N,N-diacetic acid.

Methyliminodiacetic acid can be used in the detergent compositions of the present invention excellent in adaptability to pH and is especially preferred since it imparts an excellent performance in the alkaline pH region.

As the chelate stability constant for calcium, a value of 3.7 has been reported for methyliminodiacetic acid. However, on the actual builder performance, there is a fact that methyliminodiacetic acid exceeds nitrilotriacetic acid. When molecular structure of methyliminodiacetic acid is viewed from the point of chelating performance, it is considered that the chelate stability constant for calcium increases than that of simple iminodiacetic acid due to the conversion of the amino group to tertiary amino group by the introduction of methyl group and the $Ca^{++}$ trapping power per weight increases due to its small molecular weight.

In combination with sulfonic acid surface active agents, methyliminodiacetic acid is far greater in the $Ca^{++}$ trapping power than ethylenediaminetetraacetic acid at a pH of at least 10 and, besides, it shows a surprising performance which further exceeds the performance of nitrilotriacetic acid which has been considered to have excellent performance under the same conditions.

Methylimino-N,N-diacetic acid is completely decomposed to inorganic materials in a short time in biodegradability tests such as 301C Modified MITI Test (1) described in OECD Guideline for Testing of Chemicals. Methyliminodiacetic acid is readily decomposed by microorganisms living in environmental water such as rivers, lakes, and general sewage without subjecting to activated sludge treatment and the like.

(S)-aspartic acid-N-monoacetic acid and (S)-aspartic acid-N-monopropionic acid are biodegradable builders substitutable for methyliminodiacetic acid, but although they show excellent builder performance at a pH of 10 or higher, they are inferior to methyliminodiacetic acid in $Ca^{++}$ trapping power per weight, and, hence, they must be used in a large amount. (S)-aspartic acid-N-monoacetic acid and (S)-aspartic acid-N-monopropionic acid are completely converted to inorganic materials in a short time in biodegradability tests such as 301C Modified MITI Test mentioned above. They are readily decomposed by microorganisms living in environmental water such as rivers, lakes and general sewage without subjecting to activated sludge treatment and the like.

In the above, (S)-aspartic acid-N,N-diacetic acid, taurine-N,N-diacetic acid and methyliminodiacetic acid are explained on their features as biodegradable builders. The detergent compositions containing simultaneously at least two of them as builder components can exhibit excellent performances in a wide pH condition. That is, by properly containing these builder components, performances equal to or higher than those of ethylenediaminetetraacetic acid which has hitherto been preferably used as an excellent builder can be obtained in a wide pH condition of from neutral region to alkaline region. Furthermore, it is also possible to bring out especially excellent performances under the conditions of a specific pH and a specific surface active agent by increasing the content of a specific biodegradable builder component.

In the uses such as pulp and clothing, hydrogen peroxide or organic peroxides are added for the purpose of bleaching, and builders have the function to protect these peroxides from decomposition action catalyzed by heavy metals such as iron.

In the field of food processing industry, detergent compositions containing only the builder component as a main ingredient and containing no surface active agent are sometimes used for removal of calcium carbonate, calcium oxalate and the like in washing of beer bottles, dinnerwares and plants.

The detergent compositions of the present invention may contain, as buffers, stabilizers and resticking inhibitors, general auxiliary additives, salts of silicic acid, crystalline alluminosilicic acid, laminar silicic acid and the like, salts of amino acids such as glycine, β-alanine, taurine, aspartic acid and glutamic acid, salts of polymers such as polyacrylic acid, polymaleic acid, polyaconitic acid, polyacetalcarboxylic acid, polyvinyl pyrrolidone, carboxymethylcellulose and polyethylene glycol, salts of organic acids such as citric acid, malic acid, fumaric acid, succinic acid, gluconic acid and tartaric acid, enzymes such as protease, lipase and cellulase, and salts of p-toluenesulfonic acid and sulfosuccinic acid.

There can be further added caking inhibitors such as calcium silicate, peroxide stabilizers such as magnesium silicate, antioxidants such as t-butyl-hydroxytoluene, fluorescent paints, perfumes and others. These are not limited and may be added depending on the uses.

The present invention does not preclude to use, in combination with the above builders, salts of tripolyphosphoric acid, pyrophosphoric acid and the like, salts of diethylenetriaminepentaacetic acid, ethylenediaminetetraacetic acid, nitrilotriacetic acid and the like, and others as builders. However, from the points of safety and diminishment of environmental load, it is desirable to avoid use of these conventional builders.

Next, use conditions and ratio of the components of the detergent compositions according to the present invention will be explained in detail.

In order to obtain a performance equal to or higher than that of ethylenediaminetetraacetic acid which is an excellent builder under wide use conditions, it is desired to use simultaneously at least two biodegradable builders among the three builders of (S)-aspartic acid-N,N-diacetic acid, taurine-N,N-diacetic acid and methyliminodiacetic acid. It is preferred to use (S)-aspartic acid-N,N-diacetic acid in an amount of 5–97% by weight, preferably 40–95% by weight in terms of acid, taurine-N,N-diacetic acid in an amount of 0–97% by weight, preferably 40–90% by weight in terms of acid, and methyliminodiacetic acid in an amount of 0–97% by weight, preferably 30–70% by weight in terms of acid. Desirably, the total amount of the builders is 6–810% by weight, preferably 20–240% by weight, more preferably 80–120% by weight in terms of acid based on the surface active agent component.

In case of employing such compositional ratio of the biodegradable builders, a builder performance per weight in terms of acid equal to or higher than that of ethylenediaminetetraacetic acid or nitrilotriacetic acid is developed in the pH range of 6–13 in combination with surface active agents such as of sulfonic acid type excellent in dispersibility and in the pH range of 7–12 in combination with surface active agents such as of carboxylic acid type poor in dispersibility. The builder performance here includes not only the $Ca^{++}$ trapping power, but also performances such as dispersing ability for scale or heavy metals, pH buffering ability, inhibition of dirt from resticking, inhibition of liquid detergent from setting and shape retention of solid detergent, and the builders according to the present invention also exceed nitrilotriacetic acid in these performances and performances not inferior to those of ethylenediaminetetraacetic acid and tripolyphosphoric acid can be obtained.

When conditions such as pH and surface active agent used are previously known for some uses, it is advantageous to prepare the detergent compositions with compositional ratio of the biodegradable builders suitable for these use conditions.

In many cases, household neutral detergents for kitchen and clothing are used at a pH of about 6.5–8.5 in combination with surface active agents such as dodecylbenzenesulfonates, lauryl alcohol sulfate esters and polyethylene glycol. In these uses, it is suitable to use (S)-aspartic acid-N,N-diacetic acid in an amount of 20–97% by weight, preferably 50–95% by weight in terms of acid, taurine-N,N-diacetic acid in an amount of 5–90% by weight, preferably 50–80% by weight in terms of acid, and methyliminodiacetic acid in an amount of 0–20% by weight, preferably 10–15% by weight in terms of acid on the basis of the builder composition.

Industrial detergents for cleaning of clothing, dinnerwares, plants, bottles and others are used at a pH in a wide range from neutral to strongly alkaline conditions. Especially, in the uses under alkaline condition of pH 9–13, it is suitable to use (S)-aspartic acid-N,N-diacetic acid in an amount of 0–90% by weight, preferably 20–50% by weight in terms of acid, taurine-N,N-diacetic acid in an amount of 5–90% by weight, preferably 50–80% by weight in terms of acid, and methyliminodiacetic acid in an amount of 20–97% by weight, preferably 60–90% by weight in terms of acid on the basis of the builder composition.

However, even in the uses of industrial detergents under alkaline condition of pH 9–13, when surface active agents such as laurates inferior in dispersibility are used, it is favorable to use (S)-aspartic acid-N,N-diacetic acid in an amount of 20–95% by weight, preferably 50–90% by weight in terms of acid, taurine-N,N-diacetic acid in an amount of 5–90% by weight, preferably 50–80% by weight in terms of acid, and methyliminodiacetic acid in an amount of 0–20% by weight, preferably 10–15% by weight in terms of acid on the basis of the builder composition.

Furthermore, in any uses, the whole or a part of methyliminodiacetic acid which is a biodegradable builder component in the detergent composition of the present invention can be replaced with one or both of (S)-aspartic acid-N-monoacetic acid and (S)-aspartic acid-N-monopropionic acid. When (S)-aspartic acid-N-monoacetic acid is used, it is suitable to use it in an amount of 80–350% by weight, preferably 150–320% by weight in terms of acid based on the methyliminodiacetic acid. When (S)-aspartic acid-N-monopropionic acid is used, it is suitable to use it in an amount of 120–560% by weight, preferably 240–420% by weight in terms of acid based on the methyliminodiacetic acid.

The detergent composition of the present invention can also be prepared as a liquid detergent or powder detergent of high concentration by mixing, at a predetermined ratio, the chelating agent with surface active agents and others which are the constituting components and this can be diluted to a desired concentration with water at the time of use. Alternatively, these components can be added to a diluting water at a predetermined ratio.

The present invention will be explained in more detail by the following examples, which should not be construed as limiting the invention in any manner.

EXAMPLE 1

Hardening strength of a dry powder comprising 1000 g of trisodium salt of (S)-aspartic acid-N-monoacetic acid (S-ASMA-3Na) and 25.0 g of impurity salts (comprising 18.3 g of disodium aspartate, 4.0 g of disodium fumarate, 2.2 g of monosodium salt of glycine and 0.5 g of disodium malate) was expressed by compression strength after lapse of 2 months under the load of 200 [g/cm$^2$] measured by the following method which is in accordance with JIS A 1108 (method for the measurement of compression strength of concrete) and, thus, the hardening property of the powder was evaluated.

Method for the Measurement of Compression Strength (1) A test sample (500 g) is put in a poly-ethylene bag of 20 cm×20 cm in a room at a temperature of 20–30° C. and a relative humidity of 40–70%. The powder is levelled to an area of 20 cm×20 cm and air is forced out of the bag, and, then, the bag is sealed. This bag is further put in a kraft bag and this kraft bag is sealed.

(2) The kraft bag of (1) is placed horizontally on a flat plate and a plate is put thereon. Four weights of 20 kg each are put on the upper plate to apply a load of 200 [g/cm$^2$] to the test sample.

(3) With keeping the temperature of 20–30° C. and the relative humidity of 40–70%, the test sample is taken out after lapse of 2 months from the starting of application of load. Several test pieces (4 cm long×4 cm broad×2 cm high) are cut out from the sample.

(4) The test piece is loaded by a compression tester (computer controlled universal precision tester: Simadzu Autograph AGS-100B; maximum load: 100 kg; loading speed: 2 [cm/min]), and the maximum load which the tester shows when the test piece is broken is divided by sectional area of the test piece and the resulting value is employed as the compression strength.

As a result of the measurement, the test piece had a compression strength of 1.2 [kg/cm$^2$] and it was in such a state that it could be disintegrated without any special grinding treatment.

EXAMPLE 2

An experiment was conducted in the same manner as in Example 1, except for using 1000 g of trisodium salt of (S)-aspartic acid-N-monopropionic acid (S-ASMP-3Na) and 20.0 g of impurity salts (comprising 8.2 g of disodium fumarate, 6.2 g of disodium aspartate, 4.3 g of disodium iminodiacetate, 1.1 g of disodium malate and 0.2 g of trisddium nitrilotriacetate). The results are shown in Table 1.

EXAMPLE 3

An experiment was conducted in the same manner as in Example 1, except for using 1000 g of tetrasodium salt of (S)-aspartic acid-N,N-diacetic acid (S-ASDA-4Na) and 15.0 g of impurity salts (comprising 5.5 g of disodium aspartate, 3.1 g of disodium fumarate, 3.1 g of sodium salt of β-alanine, 2.4 g of disodium iminodipropionate, 0.7 g of disodium malate and 0.2 g of sodium acrylate). The results are shown in Table 1.

EXAMPLE 4

An experiment was conducted in the same manner as in Example 1, except for using 1000 g of trisodium salt of (S)-α-alanine-N,N-diacetic acid (S-ALDA-3Na) and 22.5 g of impurity salts (comprising 10.5 g of monosodium salt of α-alanine, 3.6 g of monosodium salt of glycine, 4.8 g of disodium iminodiacetate, and 3.7 g of trisodium nitrilotriacetate). The results are shown in Table 1.

EXAMPLE 5

An experiment was conducted in the same manner as in Example 1, except that the content of the impurity salts was changed to 5.0% with the composition being the same and the load applied to the test sample was 100 [g/$cm^2$]. The results are shown in Table 1.

EXAMPLE 6

An experiment was conducted in the same manner as in Example 2, except that the content of the impurity salts was changed to 6.0% with the composition being the same and the load applied to the test sample was 100 [g/$cm^2$]. The results are shown in Table 1.

EXAMPLE 7

An experiment was conducted in the same manner as in Example 3, except that the content of the impurity salts was changed to 8.0% with the composition being the same and the load applied to the test sample was 100 [g/$cm^2$]. The results are shown in Table 1.

EXAMPLE 8

An experiment was conducted in the same manner as in Example 4, except that the content of the impurity salts was changed to 7.0% with the composition being the same and the load applied to the test sample was 100 [g/$cm^2$]. The results are shown in Table 1.

EXAMPLE 9

An experiment was conducted in the same manner as in Example 1, except that the content of the impurity salts was changed to 0.3% with the composition being the same and the load applied to the test sample was 300 [g/$cm^2$]. The results are shown in Table 1.

EXAMPLE 10

An experiment was conducted in the same manner as in Example 2, except that the content of the impurity salts was changed to 0.2% with the composition being the same and the load applied to the test sample was 300 [g/$cm^2$]. The results are shown in Table 1.

EXAMPLE 11

An experiment was conducted in the same manner as in Example 3, except that the content of the impurity salts was changed to 0.4% with the composition being the same and the load applied to the test sample was 300 [g/$cm^2$]. The results are shown in Table 1.

EXAMPLE 12

An experiment was conducted in the same manner as in Example 4, except that the content of the impurity salts was changed to 0.3% with the composition thereof being the same and the load applied to the test sample was 300 [g/$cm^2$]. The results are shown in Table 1.

EXAMPLE 13

An experiment was conducted in the same manner as in Example 1, except for using 1000 g of (S)-aspartic acid-N-monoacetic acid (S-ASMA) and 30.0 g of impurity acids (comprising 20.1 g of aspartic acid, 6.0 g of fumaric acid, 3.2 g of glycine and 0.7 g of malic acid). The results are shown in Table 1.

EXAMPLE 14

An experiment was conducted in the same manner as in Example 1, except for using 1000 g of (S)-aspartic acid-N-monopropionic acid (S-ASMP) and 15.0 g of impurity acids (comprising 6.3 g of fumaric acid, 4.7 g of aspartic acid, 3.1 g of iminodiacetic acid, 0.8 g of malic acid and 0.1 g of nitrilotriacetic acid). The results are shown in Table 1.

EXAMPLE 15

An experiment was conducted in the same manner as in Example 1, except for using 1000 g of (S)-aspartic acid-N,N-diacetic acid (S-ASDA) and 20.0 g of impurity acids (comprising 8.5 g of aspartic acid, 5.3 g of fumaric acid, 3.3 g of β-alanine, 2.3 g of iminodipropionic acid, 0.5 g of malic acid and 0.1 g of acrylic acid). The results are shown in Table 1.

EXAMPLE 16

An experiment was conducted in the same manner as in Example 1, except for using 1000 g of (S)-α-alanine-N,N-diacetic acid (S-ALDA) and 24.5 g of impurity acids (comprising 11.0 g of α-alanine, 4.6 g of glycine, 5.2 g of iminodiacetic acid and 3.7 g of nitrilotriacetic acid). The results are shown in Table 1.

EXAMPLE 17

An experiment was conducted in the same manner as in Example 13, except that the content of the impurity acids was changed to 4.0% with the composition thereof being the same and the load applied to the test sample was 100 [g/$cm^2$]. The results are shown in Table 1.

EXAMPLE 18

An experiment was conducted in the same manner as in Example 14, except that the content of the impurity acids was changed to 8.0% with the composition thereof being the same and the load applied to the test sample was changed to 100 [g/$cm^2$]. The results are shown in Table 1.

EXAMPLE 19

An experiment was conducted in the same manner as in Example 15, except that the content of the impurity acids was changed to 7.0% with the composition thereof being the same and the load applied to the test sample was changed to 100 [g/$cm^2$]. The results are shown in Table 1.

EXAMPLE 20

An experiment was conducted in the same manner as in Example 16, except that the content of the impurity acids was changed to 6.0% with the composition thereof being the same and the load applied to the test sample was changed to 100 [g/$cm^2$]. The results are shown in Table 1.

EXAMPLE 21

An experiment was conducted in the same manner as in Example 13, except that the content of the impurity acids was changed to 0.2% with the composition thereof being the same and the load applied to the test sample was changed to 300 [g/$cm^2$]. The results are shown in Table 1.

EXAMPLE 22

An experiment was conducted in the same manner as in Example 14, except that the content of the impurity acids was changed to 0.3% with the composition thereof being the same and the load applied to the test sample was changed to 300 [g/$cm^2$]. The results are shown in Table 1.

EXAMPLE 23

An experiment was conducted in the same manner as in Example 15, except that the content of the impurity acids was changed to 0.5% with the composition thereof being the same and the load applied to the test sample was changed to 300 [g/$cm^2$]. The results are shown in Table 1.

EXAMPLE 24

An experiment was conducted in the same manner as in Example 16, except that the content of the impurity acids was changed to 0.4% with the composition thereof being the same and the load applied to the test sample was changed to 300 [g/$cm^2$]. The results are shown in Table 1.

EXAMPLE 25

An experiment was conducted in the same manner as in Example 1, except for using 1000 g of trisodium salt of taurine-N,N-diacetic acid (TUDA-3Na) and 25.0 g of the impurity salts (comprising 6.0 g of monosodium salt of taurine, 5.0 g of monosodium salt of glycine, 7.0 g of disodium iminodiacetate and 7.0 g of trisodium nitrilotriacetate). The results are shown in Table 1.

EXAMPLE 26

An experiment was conducted in the same manner as in Example 1, except for using 1000 g of disodium N-methyliminodiacetate (MIDA-2Na) and 20.0 g of the impurity salts (comprising 8.0 g of monosodium salt of glycine, 7.0 g of disodium iminodiacetate and 5.00 g of trisodium nitrilotriacetate). The results are shown in Table 1.

EXAMPLE 27

An experiment was conducted in the same manner as in Example 1, except for using 1000 g of trisodium salt of anthranilic acid-N,N-diacetic acid (ANTDA-3Na) and 15.0 g of the impurity salts (comprising 4.0 g of monosodium anthranilate, 3.0 g of monosodium salt of glycine, 5.0 g of disodium iminodiacetate and 3.0 g of trisodium nitrilotriacetate). The results are shown in Table 1.

EXAMPLE 28

An experiment was conducted in the same manner as in Example 25, except that the content of the impurity salts was changed to 5.0% with the composition thereof being the same and the load applied to the test sample was changed to 100 [g/$cm^2$]. The results are shown in Table 1.

EXAMPLE 29

An experiment was conducted in the same manner as in Example 26, except that the content of the impurity salts was changed to 6.0% with the composition thereof being the same and the load applied to the test sample was changed to 100 [g/$cm^2$]. The results are shown in Table 1.

EXAMPLE 30

An experiment was conducted in the same manner as in Example 27, except that the content of the impurity salts was changed to 8.0% with the composition thereof being the same and the load applied to the test sample was changed to 100 [g/$cm^2$]. The results are shown in Table 1.

EXAMPLE 31

An experiment was conducted in the same manner as in Example 25, except that the content of the impurity salts was changed to 0.3% with the composition thereof being the same and the load applied to the test sample was changed to 300 [g/$cm^2$]. The results are shown in Table 1.

EXAMPLE 32

An experiment was conducted in the same manner as in Example 26, except that the content of the impurity salts was changed to 0.2% with the composition thereof being the same and the load applied to the test sample was changed to 300 [g/$cm^2$]. The results are shown in Table 1.

EXAMPLE 33

An experiment was conducted in the same manner as in Example 27, except that the content of the impurity salts was changed to 0.4% with the composition thereof being the same and the load applied to the test sample was changed to 300 [g/$cm^2$]. The results are shown in Table 1.

EXAMPLE 34

An experiment was conducted in the same manner as in Example 1, except for using 1000 g of taurine-N,N-diacetic acid (TUDA) and 25.0 g of the impurity acids (comprising 6.0 g of taurine, 5.0 g of glycine, 7.0 g of iminodiacetic acid and 7.0 g of nitrilotriacetic acid). The results are shown in Table 1.

EXAMPLE 35

An experiment was conducted in the same manner as in Example 1, except for using 1000 g of N-methyliminodiacetic acid (MIDA) and 20.0 g of the impurity acids (comprising 8.0 g of glycine, 1.0 g of iminodiacetic acid and 5.00 g of nitrilotriacetic acid). The results are shown in Table 1.

EXAMPLE 36

An experiment was conducted in the same manner as in Example 1, except for using 1000 g of anthranilic acid-N, N-diacetic acid (ANTDA) and 15.0 g of the impurity acids (comprising 4.0 g of anthranilic acid, 3.0 g of glycine, 5.0 g of iminodiacetic acid and 3.0 g of nitrilotriacetic acid). The results are shown in Table 1.

EXAMPLE 37

An experiment was conducted in the same manner as in Example 34, except that the content of the impurity acids was changed to 4.0% with the composition thereof being the same and the load applied to the test sample was changed to 100 [g/cm$^2$]. The results are shown in Table 1.

EXAMPLE 38

An experiment was conducted in the same manner as in Example 35, except that the content of the impurity acids was changed to 8.0% with the composition thereof being the same and the load applied to the test sample was changed to 100 [g/cm$^2$]. The results are shown in Table 1.

EXAMPLE 39

An experiment was conducted in the same manner as in Example 36, except that the content of the impurity acids was changed to 7.0% with the composition thereof being the same and the load applied to the test sample was changed to 100 [g/cm$^2$]. The results are shown in Table 1.

EXAMPLE 40

An experiment was conducted in the same manner as in Example 34, except that the content of the impurity acids was changed to 0.2% with the composition thereof being the same and the load applied to the sample was changed to 300 [g/cm$^2$]. The results are shown in Table 1.

EXAMPLE 41

An experiment was conducted in the same manner as in Example 35, except that the content of the impurity acids was changed to 0.3% with the composition thereof being the same and the load applied to the test sample was changed to 300 [g/cm$^2$]. The results are shown in Table 1.

EXAMPLE 42

An experiment was conducted in the same manner as in Example 36, except that the content of the impurity acids was changed to 0.5% with the composition thereof being the same and the load applied to the test sample was changed to 300 [g/cm$^2$]. The results are shown in Table 1.

EXAMPLE 43

An experiment was conducted in the same manner as in Example 1, except for using 1000 g of iron salt of anthranilic acid-N,N-diacetic acid (ANTDA-Fe) and 15.0 g of the impurity Fe salts (comprising 4.0 g of anthranilate, 3.0 g of salt of glycine, 5.0 g of iminodiacetate and 3.0 g of nitrilotriacetate). The results are shown in Table 1.

EXAMPLE 44

An experiment was conducted in the same manner as in Example 43, except that the content of the impurity salts was changed to 5.0% with the composition thereof being the same and the load applied to the test sample was changed to 100 [g/cm$^2$]. The results are shown in Table 1.

EXAMPLE 45

An experiment was conducted in the same manner as in Example 43, except that the content of the impurity salts was changed to 0.3% with the composition thereof being the same and the load applied to the test sample was changed to 300 [g/cm$^2$]. The results are shown in Table 1.

COMPARATIVE EXAMPLE 1

An experiment was conducted in the same manner as in Example 1, except that the content of the impurity salts was changed to 10% with the composition thereof being the same and the load applied to the test sample was changed to 100 [g/cm$^2$]. The results are shown in Table 2.

COMPARATIVE EXAMPLE 2

An experiment was conducted in the same manner as in Example 2, except that the content of the impurity salts was changed to 15% with the composition thereof being the same and the load applied to the test sample was changed to 100 [g/cm$^2$]. The results are shown in Table 2.

COMPARATIVE EXAMPLE 3

An experiment was conducted in the same manner as in Example 3, except that the content of the impurity salts was changed to 20% with the composition thereof being the same and the load applied to the test sample was changed to 100 [g/cm$^2$]. The results are shown in Table 2.

COMPARATIVE EXAMPLE 4

An experiment was conducted in the same manner as in Example 4, except that the content of the impurity salts was changed to 18% with the composition being the same and the load applied to the test sample was changed to 100 [g/cm$^2$]. The results are shown in Table 2.

COMPARATIVE EXAMPLE 5

An experiment was conducted in the same manner as in Example 13, except that the content of the impurity acids was changed to 30% with the composition thereof being the same and the load applied to the test sample was changed to 100 [g/cm$^2$]. The results are shown in Table 2.

COMPARATIVE EXAMPLE 6

An experiment was conducted in the same manner as in Example 14, except that the content of the impurity salts was changed to 20% with the composition thereof being the same and the load applied to the sample was changed to 100 [g/cm$^2$]. The results are shown in Table 2.

COMPARATIVE EXAMPLE 7

An experiment was conducted in the same manner as in Example 15, except that the content of the impurity salts was changed to 15% with the composition thereof being the same and the load applied to the test sample was changed to 100 [g/cm$^2$]. The results are shown in Table 2.

COMPARATIVE EXAMPLE 8

An experiment was conducted in the same manner as in Example 16, except that the content of the impurity salts was changed to 23% with the composition thereof being the same and the load applied to the sample was changed to 100 [g/cm$^2$]. The results are shown in Table 2.

COMPARATIVE EXAMPLE 9

An experiment was conducted in the same manner as in Example 25, except that the content of the impurity salts was changed to 10% with the composition thereof being the same and the load applied to the sample was changed to 100 [g/$cm^2$]. The results are shown in Table 2.

COMPARATIVE EXAMPLE 10

An experiment was conducted in the same manner as in Example 26, except that the content of the impurity salts was changed to 15% with the composition thereof being the same and the load applied to the sample was changed to 100 [g/$cm^2$]. The results are shown in Table 2.

COMPARATIVE EXAMPLE 11

An experiment was conducted in the same manner as in Example 27, except that the content of the impurity salts was changed to 20% with the composition thereof being the same and the load applied to the sample was changed to 100 [g/$cm^2$]. The results are shown in Table 2.

COMPARATIVE EXAMPLE 12

An experiment was conducted in the same manner as in Example 34, except that the content of the impurity acids was changed to 30% with the composition thereof being the same and the load applied to the sample was changed to 100 [g/$cm^2$]. The results are shown in Table.

COMPARATIVE EXAMPLE 13

An experiment was conducted in the same manner as in Example 35, except that the content of the impurity salts was changed to 20% with the composition thereof being the same and the load applied to the test sample was changed to 100 [g/$cm^2$]. The results are shown in Table 2.

COMPARATIVE EXAMPLE 14

An experiment was conducted in the same manner as in Example 36, except that the content of the impurity salts was changed to 15% with the composition thereof being the same and the load applied to the test sample was changed to 100 [g/$cm^2$]. The results are shown in Table 2.

COMPARATIVE EXAMPLE 15

An experiment was conducted in the same manner as in Example 43, except that the content of the impurity salts was changed to 15% with the composition thereof being the same and the load applied to the test sample was changed to 100 [g/$cm^2$]. The results are shown in Table 2.

TABLE 1

| Example | Compound of the formula [I] | Content of impurity [wt. %] | Load [Kg] | Compression strength after stored for 2 months [Kg/$cm^2$] |
|---|---|---|---|---|
| 1 | S-ASMA-3Na | 2.4 | 200 | 1.2 |
| 2 | S-ASMP-3Na | 2.0 | 200 | 1.0 |
| 3 | S-ASDA-4Na | 1.5 | 200 | 0.9 |
| 4 | S-ALDA-3Na | 2.2 | 200 | 1.1 |
| 5 | S-ASMA-3Na | 5.0 | 100 | 1.2 |
| 6 | S-ASMP-3Na | 6.0 | 100 | 1.2 |
| 7 | S-ASDA-4Na | 8.0 | 100 | 1.3 |
| 8 | S-ALDA-3Na | 7.0 | 100 | 1.0 |
| 9 | S-ASMA-3Na | 0.3 | 300 | 0.8 |
| 10 | S-ASMP-3Na | 0.2 | 300 | 1.0 |
| 11 | S-ASDA-4Na | 0.4 | 300 | 0.8 |
| 12 | S-ALDA-3Na | 0.3 | 300 | 0.9 |
| 13 | S-ASMA | 2.9 | 200 | 1.1 |

TABLE 1-continued

| Example | Compound of the formula [I] | Content of impurity [wt. %] | Load [Kg] | Compression strength after stored for 2 months [Kg/$cm^2$] |
|---|---|---|---|---|
| 14 | S-ASMP | 1.5 | 200 | 0.6 |
| 15 | S-ASDA | 2.0 | 200 | 0.9 |
| 16 | S-ALDA | 2.4 | 200 | 0.8 |
| 17 | S-ASMA | 4.0 | 100 | 0.9 |
| 18 | S-ASMP | 8.0 | 100 | 1.2 |
| 19 | S-ASDA | 7.0 | 100 | 1.1 |
| 20 | S-ALDA | 6.0 | 100 | 1.0 |
| 21 | S-ASMA | 0.2 | 300 | 0.8 |
| 22 | S-ASMP | 0.3 | 300 | 0.9 |
| 23 | S-ASDA | 0.5 | 300 | 1.0 |
| 24 | S-ALDA | 0.4 | 300 | 0.9 |
| 25 | TUDA-3Na | 2.4 | 200 | 1.1 |
| 26 | MIDA-2Na | 2.0 | 200 | 1.2 |
| 27 | ANTDA-3Na | 1.5 | 200 | 1.0 |
| 28 | TUDA-3Na | 5.0 | 100 | 1.3 |
| 29 | MIDA-2Na | 6.0 | 100 | 1.2 |
| 30 | ANTDA-3Na | 8.0 | 100 | 1.2 |
| 31 | TUDA-3Na | 0.3 | 300 | 1.0 |
| 32 | MIDA-2Na | 0.2 | 300 | 0.8 |
| 33 | ANTDA-3Na | 0.4 | 300 | 0.9 |
| 34 | TUDA | 2.9 | 200 | 1.2 |
| 35 | MIDA | 1.5 | 200 | 0.8 |
| 36 | ANTDA | 2.0 | 200 | 0.9 |
| 37 | TUDA | 4.0 | 100 | 1.0 |
| 38 | MIDA | 8.0 | 100 | 1.1 |
| 39 | ANTDA | 7.0 | 100 | 1.2 |
| 40 | TUDA | 0.2 | 300 | 0.9 |
| 41 | MIDA | 0.3 | 300 | 1.0 |
| 42 | ANTDA | 0.5 | 300 | 1.1 |
| 43 | ANTDA-Fe | 1.5 | 200 | 0.9 |
| 44 | ANTDA-Fe | 5.0 | 100 | 1.0 |
| 45 | ANTDA-Fe | 0.3 | 300 | 0.8 |

TABLE 2

| Comparative Example | Compound of the formula [I] | Content of impurity [wt. %] | Load [Kg] | Compression strength after stored for 2 months [Kg/$cm^2$] |
|---|---|---|---|---|
| 1 | S-ASMA-3Na | 10 | 100 | 2.6 |
| 2 | S-ASMP-3Na | 15 | 100 | 3.0 |
| 3 | S-ASDA-4Na | 20 | 100 | 3.2 |
| 4 | S-ALDA-3Na | 18 | 100 | 2.8 |
| 5 | S-ASMA | 30 | 100 | 2.8 |
| 6 | S-ASMP | 20 | 100 | 2.5 |
| 7 | S-ASDA | 15 | 100 | 2.3 |
| 8 | S-ALDA | 23 | 100 | 2.6 |
| 9 | TUDA-3Na | 10 | 100 | 2.5 |
| 10 | MIDA-2Na | 15 | 100 | 2.6 |
| 11 | ANTDA-3Na | 20 | 100 | 2.5 |
| 12 | TUDA | 30 | 100 | 3.3 |
| 13 | MIDA | 20 | 100 | 2.7 |
| 14 | ANTDA | 15 | 100 | 2.5 |
| 15 | ANTDA-Fe | 15 | 100 | 2.5 |

It can be seen from these examples that when the impurity acids or salts thereof were present in an amount larger than 8% based on the compound of the formula [1], hardening of the stored powder increased and, at the same time, the compression strength increased. When the impurity acids or salts thereof were present in an amount of at most 8%, such increase in hardening property of the stored powder and increase in compression strength were not seen.

EXAMPLE 46

An experiment was conducted in the same manner as in Example 1, except for using 1000 g of tetrasodium ethylenediaminedisuccinate (EDDS-4Na) and 25.0 g of the impurity salts (comprising 8.0 g of disodium maleate, 9.0 g of disodium fumarate, 5.0 g of disodium ethylenediaminemonosuccinate and 3.0 g of disodium malate). The results are shown in Table 3.

EXAMPLE 47

An experiment was conducted in the same manner as in Example 1, except for using 1000 g of tetrasodium (S,S)-ethylenediaminedisuccinate (SS-EDDS-4Na) and 20.0 g of impurity salts (comprising 5.0 g of disodium (S)-aspartate, 5.0 g of disodium (S)-N-(2-hydroxyethyl)-aspartate, 5.0 g of tetrasodium (S,S)-N-(2-hydroxyethyl)-ethylenediaminedisuccinate and 5.0 g of disodium fumarate). The results are shown in Table 3.

EXAMPLE 48

An experiment was conducted in the same manner as in Example 1, except for using 1000 g of tetrasodium 1,3-propanediaminedisuccinate (PDDS-4Na) and 15.0 g of the impurity salts (comprising 5.0 g of disodium maleate, 4.0 g of disodium fumarate, 3.0 g of disodium 1,3-propanediaminemonosuccinate and 3.0 g of disodium malate). The results are shown in Table 3.

EXAMPLE 49

An experiment was conducted in the same manner as in Example 1, except for using 1000 g of tetrasodium (S,S)-1,3-propanediaminedisuccinate (SS-PDDS-4Na) and 20.0 g of impurity salts (comprising 5.0 g of disodium (S)-aspartate, 5.0 g of disodium (S)-3-hydroxypropylaspartate, 5.0 g of tetrasodium (S,S)-3-hydroxypropyl-1,3-propanediaminedisuccinate and 5.0 g of disodium fumarate). The results are shown in Table 3.

EXAMPLE 50

An experiment was conducted in the same manner as in Example 1, except for using 1000 g of tetrasodium (S,S)-2-hydroxy-1,3-propanediaminedisuccinate (SS-PDDS-OH-4Na) and 25.0 g of impurity salts (comprising 15.0 g of disodium (S)-aspartate, 5.0 g of disodium (S)-N-(1,2-dihydroxypropyl)-aspartate and 5.0 g of disodium fumarate). The results are shown in Table 3.

EXAMPLE 51

An experiment was conducted in the same manner as in Example 46, except that the content of the impurity salts was changed to 5.0% with the composition thereof being the same and the load applied to the test sample was changed to 100 [$g/cm^2$]. The results are shown in Table 3.

EXAMPLE 52

An experiment was conducted in the same manner as in Example 47, except that the content of the impurity salts was changed to 6.0% with the composition being the same and the load applied to the test sample was changed to 100 [$g/cm^2$]. The results are shown in Table 3.

EXAMPLE 53

An experiment was conducted in the same manner as in Example 48, except that the content of the impurity salts was changed to 8.0% with the composition being the same and the load applied to the test sample was changed to 100 [$g/cm^2$]. The results are shown in Table 3.

EXAMPLE 54

An experiment was conducted in the same manner as in Example 49, except that the content of the impurity salts was changed to 6.0% with the composition being the same and the load applied to the test sample was changed to 100 [$g/cm^2$]. The results are shown in Table 3.

EXAMPLE 55

An experiment was conducted in the same manner as in Example 50, except that the content of the impurity salts was changed to 8.0% with the composition being the same and the load applied to the test sample was changed to 100 [$g/cm^2$]. The results are shown in Table 3.

EXAMPLE 56

An experiment was conducted in the same manner as in Example 46, except that the content of the impurity salts was changed to 0.3% with the composition being the same and the load applied to the test sample was changed to 300 [$g/cm^2$]. The results are shown in Table 3.

EXAMPLE 57

An experiment was conducted in the same manner as in Example 47, except that the content of the impurity salts was changed to 0.2% with the composition being the same and the load applied to the test sample was changed to 300 [$g/cm^2$]. The results are shown in Table 3.

EXAMPLE 58

An experiment was conducted in the same manner as in Example 48, except that the content of the impurity salts was changed to 0.4% with the composition thereof being the same and the load applied to the test sample was changed to 300 [$g/cm^2$]. The results are shown in Table 3.

EXAMPLE 59

An experiment was conducted in the same manner as in Example 49, except that the content of the impurity salts was changed to 0.2% with the composition thereof being the same and the load applied to the test sample was changed to 300 [$g/cm^2$]. The results are shown in Table 3.

EXAMPLE 60

An experiment was conducted in the same manner as in Example 50, except that the content of the impurity salts was changed to 0.4% with the composition thereof being the same and the load applied to the test sample was changed to 300 [$g/cm^2$]. The results are shown in Table 3.

EXAMPLE 61

An experiment was conducted in the same manner as in Example 1, except for using 1000 g of ethylenediaminedisuccinic acid (EDDS) and 25.0 g of impurity acids (comprising 8.0 g of maleic acid, 9.0 g of fumaric acid, 5.0 g of ethylenediaminemonosuccinic acid and 3.0 g of malic acid). The results are shown in Table 3.

EXAMPLE 62

An experiment was conducted in the same manner as in Example 1, except for using 1000 g of (S,S)-ethylenediaminedisuccinic acid (SS-EDDS) and 20.0 g of impurity acids (comprising 5.0 g of (S)-aspartic acid, 5.0 g of (S)-N-(2-hydroxyethyl)-aspartic acid, 5.0 g of (S,S)-N-

(2-hydroxyethyl)-ethylenediaminedisuccinic acid and 5.0 g of fumaric acid). The results are shown in Table 3.

EXAMPLE 63

An experiment was conducted in the same manner as in Example 1, except for using 1000 g of 1,3-propanediaminedisuccinic acid (PDDS) and 15.0 g of impurity acids (comprising 5.0 g of maleic acid, 4.0 g of fumaric acid, 3.0 g of 1,3-propanediaminemonosuccinic acid and 3.0 g of malic acid). The results are shown in Table 3.

EXAMPLE 64

An experiment was conducted in the same manner as in Example 1, except for using 1000 g of (S,S)-1,3-propanediaminedisuccinic acid (SS-PDDS) and 20.0 g of impurity acids (comprising 5.0 g of (S)-aspartic acid, 5.0 g of (S)-3-hydroxypropylaspartic acid, 5.0 g of (S,S)-3-hydroxypropyl-1,3-propanediaminedisuccinic acid and 5.0 g of fumaric acid). The results are shown in Table 3.

EXAMPLE 65

An experiment was conducted in the same manner as in Example 1, except for using 1000 g of (S,S)-2-hydroxy-1,3-propanediaminedisuccinic acid (SS-PDDS-OH) and 25.0 g of impurity acids (comprising 15.0 g of (S)-aspartic acid, 5.0 g of (S)-N-(1,2-dihydroxypropyl)-aspartic acid and 5.0 g of fumaric acid). The results are shown in Table 3.

EXAMPLE 66

An experiment was conducted in the same manner as in Example 61, except that the content of the impurity acids was changed to 5.0% with the composition thereof being the same and the load applied to the test sample was changed to 100 [g/cm$^2$]. The results are shown in Table 3.

EXAMPLE 67

An experiment was conducted in the same manner as in Example 62, except that the content of the impurity acids was changed to 6.0% with the composition thereof being the same and the load applied to the test sample was changed to 100 [g/cm$^2$]. The results are shown in Table 3.

EXAMPLE 68

An experiment was conducted in the same manner as in Example 63, except that the content of the impurity acids was changed to 8.0% with the composition thereof being the same and the load applied to the test sample was changed to 100 [g/cm$^2$]. The results are shown in Table 3.

EXAMPLE 69

An experiment was conducted in the same manner as in Example 64, except that the content of the impurity acids was changed to 6.0% with the composition thereof being the same and the load applied to the test sample was changed to 100 [g/cm$^2$]. The results are shown in Table 3.

EXAMPLE 70

An experiment was conducted in the same manner as in Example 65, except that the content of the impurity acids was changed to 8.0% with the composition thereof being the same and the load applied to the test sample was changed to 100 [g/cm$^2$]. The results are shown in Table 3.

EXAMPLE 71

An experiment was conducted in the same manner as in Example 61, except that the content of the impurity acids was changed to 0.3% with the composition thereof being the same and the load applied to the test sample was changed to 300 [g/cm$^2$]. The results are shown in Table 3.

EXAMPLE 72

An experiment was conducted in the same manner as in Example 62, except that the content of the impurity acids was changed to 0.2% with the composition thereof being the same and the load applied to the test sample was changed to 300 [g/cm$^2$]. The results are shown in Table 3.

EXAMPLE 73

An experiment was conducted in the same manner as in Example 63, except that the content of the impurity acids was changed to 0.4% with the composition thereof being the same and the load applied to the test sample was changed to 300 [g/cm$^2$]. The results are shown in Table 3.

EXAMPLE 74

An experiment was conducted in the same manner as in Example 64, except that the content of the impurity acids was changed to 0.2% with the composition thereof being the same and the load applied to the test sample was changed to 300 [g/cm$^2$]. The results are shown in Table 3.

EXAMPLE 75

An experiment was conducted in the same manner as in Example 65, except that the content of the impurity acids was changed to 0.4% with the composition thereof being the same and the load applied to the test sample was changed to 300 [g/cm$^2$]. The results are shown in Table 3.

EXAMPLE 76

An experiment was conducted in the same manner as in Example 1, except for using 1000 g of iron ammonium ethylenediaminedisuccinate (EDDS-Fe—$NH_4$) and 25.0 g of impurity ammonium salts (comprising 8.0 g of maleate, 9.0 g of fumarate, 5.0 g of ethylenediaminemonosuccinate and 3.0 g of malate). The results are shown in Table 3.

EXAMPLE 77

An experiment was conducted in the same manner as in Example 1, except for using 1000 g of copper disodium ethylenediaminedisuccinate (EDDS-Cu-2Na) and 25.0 g of impurity sodium salts (comprising 8.0 g of maleate, 9.0 g of fumarate, 5.0 g of ethylenediaminemonosuccinate and 3.0 g of malate). The results are shown in Table 3.

EXAMPLE 78

An experiment was conducted in the same manner as in Example 1, except for using 1000 g of nickel disodium ethylenediaminedisuccinate (EDDS-Ni-2Na) and 25.0 g of impurity sodium salts (comprising 8.0 g of maleate, 9.0 g of fumarate, 5.0 g of ethylenediaminemonosuccinate and 3.0 g of malate). The results are shown in Table 3.

EXAMPLE 79

An experiment was conducted in the same manner as in Example 1, except for using 1000 g of iron ammonium (S,S)-ethylenediaminedisuccinate (SS-EDDS-Fe—$NH_4$) and 20.0 g of impurity ammonium salts (comprising 5.0 g of (S)-aspartate, 5.0 g of (S)-N-(2-hydroxyethyl)-aspartate, 5.0 g of (S,S)-N-(2-hydroxyethyl)ethylenediaminedisuccinate and 5.0 g of fumarate). The results are shown in Table 3.

EXAMPLE 80

An experiment was conducted in the same manner as in Example 1, except for using 1000 g of copper disodium (S,S)-ethylenediaminedisuccinate (SS-EDDS-Cu-2Na) and 20.0 g of impurity sodium salts (comprising 5.0 g of (S)-aspartate, 5.0 g of (S)-N-(2-hydroxyethyl)-aspartate, 5.0 g of (S,S)-N-(2-hydroxyethyl)-ethylenediaminedisuccinate and 5.0 g of fumarate). The results are shown in Table 3.

EXAMPLE 81

An experiment was conducted in the same manner as in Example 1, except for using 1000 g of nickel disodium (S,S)-ethylenediaminedisuccinate (SS-EDDS-Ni-2Na) and 20.0 g of impurity sodium salts (comprising 5.0 g of (S)-aspartate, 5.0 g of (S)-N-(2-hydroxyethyl)-aspartate, 5.0 g of (S,S)-N-(2-hydroxyethyl)-ethylenediaminedisuccinate and 5.0 g of fumarate). The results are shown in Table 3.

EXAMPLE 82

An experiment was conducted in the same manner as in Example 1, except for using 1000 g of iron ammonium (S,S)-1,3-propanediaminedisuccinate (SS-PDDS-Fe—$NH_4$) and 20.0 g of impurity ammonium salts (comprising 5.0 g of (S)-aspartate, 5.0 g of (S)-3-hydroxypropylaspartate, 5.0 g of (S,S)-3-hydroxypropyl-1,3-propanediaminedisuccinate and 5.0 g of fumarate). The results are shown in Table 3.

EXAMPLE 83

An experiment was conducted in the same manner as in Example 1, except for using 1000 g of copper disodium (S,S)-1,3-propanediaminedisuccinate (SS-PDDS-Cu-2Na) and 20.0 g of impurity sodium salts (comprising 5.0 g of (S)-aspartate, 5.0 g of (S)-3-hydroxypropylaspartate, 5.0 g of (S,S)-3-hydroxypropyl-1,3-propanediaminedisuccinate and 5.0 g of fumarate). The results are shown in Table 3.

EXAMPLE 84

An experiment was conducted in the same manner as in Example 1, except for using 1000 g of nickel disodium (S,S)-1,3-propanediaminedisuccinate (SS-PDDS-Ni-2Na) and 20.0 g of impurity sodium salts (comprising 5.0 g of (S)-aspartate, 5.0 g of (S)-3-hydroxypropylaspartate, 5.0 g of (S,S)-3-hydroxypropyl-1,3-propanediaminedisuccinate and 5.0 g of fumarate). The results are shown in Table 3.

COMPARATIVE EXAMPLE 16

An experiment was conducted in the same manner as in Example 46, except that the content of the impurity salts was changed to 10% with the composition thereof being the same and the load applied to the test sample was changed to 100 [g/$cm^2$]. The results are shown in Table 4.

COMPARATIVE EXAMPLE 17

An experiment was conducted in the same manner as in Example 47, except that the content of the impurity salts was changed to 15% with the composition thereof being the same and the load applied to the test sample was changed to 100 [g/$cm^2$]. The results are shown in Table 4.

COMPARATIVE EXAMPLE 18

An experiment was conducted in the same manner as in Example 48, except that the content of the impurity salts was changed to 20% with the composition thereof being the same and the load applied to the test sample was changed to 100 [g/$cm^2$]. The results are shown in Table 4.

COMPARATIVE EXAMPLE 19

An experiment was conducted in the same manner as in Example 49, except that the content of the impurity acids was changed to 30% with the composition thereof being the same and the load applied to the test sample was changed to 100 [g/$cm^2$]. The results are shown in Table 4.

COMPARATIVE EXAMPLE 20

An experiment was conducted in the same manner as in Example 50, except that the content of the impurity salts was changed to 20% with the composition thereof being the same and the load applied to the test sample was changed to 100 [g/$cm^2$]. The results are shown in Table 4.

COMPARATIVE EXAMPLE 21

An experiment was conducted in the same manner as in Example 61, except that the content of the impurity salts was changed to 15% with the composition thereof being the same and the load applied to the sample was changed to 100 [g/$cm^2$]. The results are shown in Table 4.

COMPARATIVE EXAMPLE 22

An experiment was conducted in the same manner as in Example 62, except that the content of the impurity salts was changed to 15% with the composition thereof being the same and the load applied to the test sample was changed to 100 [g/$cm^2$]. The results are shown in Table 4.

COMPARATIVE EXAMPLE 23

An experiment was conducted in the same manner as in Example 63, except that the content of the impurity salts was changed to 10% with the composition thereof being the same and the load applied to the test sample was changed to 100 [g/$cm^2$]. The results are shown in Table 4.

COMPARATIVE EXAMPLE 24

An experiment was conducted in the same manner as in Example 64, except that the content of the impurity salts was changed to 15% with the composition thereof being the same and the load applied to the test sample was changed to 100 [g/$cm^2$]. The results are shown in Table 4.

COMPARATIVE EXAMPLE 25

An experiment was conducted in the same manner as in Example 65, except that the content of the impurity salts was changed to 20% with the composition thereof being the same and the load applied to the test sample was changed to 100 [g/$cm^2$]. The results are shown in Table 4.

COMPARATIVE EXAMPLE 26

An experiment was conducted in the same manner as in Example 79, except that the content of the impurity acids was changed to 30% with the composition thereof being the same and the load applied to the test sample was changed to 100 [g/$cm^2$]. The results are shown in Table 4.

COMPARATIVE EXAMPLE 27

An experiment was conducted in the same manner as in Example 80, except that the content of the impurity salts was changed to 20% with the composition thereof being the same and the load applied to the test sample was changed to 100 [g/cm$^2$]. The results are shown in Table 4.

COMPARATIVE EXAMPLE 28

An experiment was conducted in the same manner as in Example 81, except that the content of the impurity salts was changed to 15% with the composition thereof being the same and the load applied to the test sample was changed to 100 [g/cm$^2$]. The results are shown in Table 4.

TABLE 3

| Example | Compound of the formula [I] | Content of impurity [wt. %] | Load [Kg] | Compression strength after stored for 2 months [Kg/cm$^2$] |
|---|---|---|---|---|
| 46 | EDDS-4Na | 2.4 | 200 | 1.1 |
| 47 | SS-EDDS-4Na | 2.0 | 200 | 1.2 |
| 48 | PDDS-4Na | 1.5 | 200 | 1.0 |
| 49 | SS-PDDS-4Na | 2.0 | 200 | 1.3 |
| 50 | PDDS-OH-4Na | 2.4 | 200 | 1.2 |
| 51 | EDDS-4Na | 5.0 | 100 | 1.2 |
| 52 | SS-EDDS-4Na | 6.0 | 100 | 1.0 |
| 53 | PDDS-4Na | 8.0 | 100 | 0.8 |
| 54 | SS-PDDS-4Na | 6.0 | 100 | 0.9 |
| 55 | PDDS-OH-4Na | 8.0 | 100 | 1.2 |
| 56 | EDDS-4Na | 0.3 | 300 | 0.8 |
| 57 | SS-EDDS-4Na | 0.2 | 300 | 0.9 |
| 58 | PDDS-4Na | 0.4 | 300 | 1.0 |
| 59 | SS-PDDS-4Na | 0.2 | 300 | 1.1 |
| 60 | PDDS-OH-4Na | 0.4 | 300 | 1.2 |
| 61 | EDDS | 2.4 | 200 | 0.9 |
| 62 | SS-EDDS | 2.0 | 200 | 1.0 |
| 63 | PDDS | 1.5 | 200 | 1.1 |
| 64 | SS-PDDS | 2.0 | 200 | 0.9 |
| 65 | PDDS-OH | 2.4 | 200 | 1.0 |
| 66 | EDDS | 5.0 | 100 | 0.8 |
| 67 | SS-EDDS | 6.0 | 100 | 1.1 |
| 68 | PDDS | 8.0 | 100 | 1.2 |
| 69 | SS-PDDS | 6.0 | 100 | 1.0 |
| 70 | PDDS-OH | 8.0 | 100 | 0.8 |
| 71 | EDDS | 0.3 | 300 | 1.2 |
| 72 | SS-EDDS | 0.2 | 300 | 1.3 |
| 73 | PDDS | 0.4 | 300 | 1.1 |
| 74 | SS-PDDS | 0.2 | 300 | 1.2 |
| 75 | PDDS-OH | 0.4 | 300 | 1.0 |
| 76 | EDDS-Fe-NH4 | 2.4 | 200 | 1.1 |
| 77 | EDDS-Cu-2Na | 2.4 | 200 | 1.2 |
| 78 | EDDS-Ni-2Na | 2.0 | 200 | 1.0 |
| 79 | SS-EDDS-Fe-$NH_4$ S | 2.0 | 200 | 0.9 |
| 80 | S-EDDS-Cu-2Na S | 2.0 | 200 | 1.0 |
| 81 | S-EDDS-Ni-2Na S | 2.0 | 200 | 1.2 |
| 82 | S-PDDS-Fe-2$NH_4$ S | 2.0 | 200 | 1.1 |
| 83 | S-PDDS-Cu-2Na S | 2.0 | 200 | 1.3 |
| 84 | S-PDDS-Ni-2Na | 2.0 | 200 | 1.0 |

TABLE 4

| Comparative Example | Compound of the formula [I] | Content of impurity [wt. %] | Load [Kg] | Compression strength after stored for 2 months [Kg/cm$^2$] |
|---|---|---|---|---|
| 16 | EDDS-4Na | 10 | 100 | 2.8 |
| 17 | SS-EDDS-4Na | 15 | 100 | 2.9 |
| 18 | PDDS-4Na | 20 | 100 | 3.0 |
| 19 | SS-PDDS-4Na | 30 | 100 | 2.9 |
| 20 | SS-PDDS-OH-4Na | 20 | 100 | 2.7 |
| 21 | EDDS | 15 | 100 | 2.8 |
| 22 | SS-EDDS | 15 | 100 | 2.5 |
| 23 | PDDS | 10 | 100 | 2.7 |
| 24 | SS-PDDS | 15 | 100 | 2.8 |
| 25 | SS-PDDS-OH | 20 | 100 | 2.5 |

TABLE 4-continued

| Comparative Example | Compound of the formula [I] | Content of impurity [wt. %] | Load [Kg] | Compression strength after stored for 2 months [Kg/cm$^2$] |
|---|---|---|---|---|
| 26 | SS-EDDS-Fe-$NH_4$ | 30 | 100 | 2.7 |
| 27 | SS-EDDS-Cu-2Na | 20 | 100 | 2.8 |
| 28 | SS-EDDS-Ni | 15 | 100 | 2.5 |

EXAMPLE 85

A dry powder comprising 1000 g of trisodium salt of (S)-aspartic acid-N-monoacetic acid (ASMA-3Na) and 250 g of impurity salts (comprising 183 g of disodium aspartate, 40 g of disodium fumarate, 22 g of monosodium salt of glycine and 5 g of disodium malate) was dissolved in 1500 g of water in a stainless steel vessel externally provided with a thermoelectric heater to prepare a transparent aqueous solution with a light yellow color. This aqueous solution was kept at 50° C. for 60 days, and, then, the components were analyzed by HPLC and, simultaneously, the appearance of the solution was observed. The results are shown in Table 5.

EXAMPLE 86

An experiment was conducted in the same manner as in Example 85, except for using 1000 g of tetrasodium salt of (S)-aspartic acid-N,N-diacetic acid (ASDA-4Na) and 200 g of impurity salts (comprising 82 g of disodium fumarate, 62 g of disodium aspartate, 43 g of disodium iminodiacetate, 11 g of disodium malate and 2 g of trisodium nitrilotriacetate). The results are shown in Table 5.

EXAMPLE 87

An experiment was conducted in the same manner as in Example 85, except for using 1000 g of trisodium salt of (S)-aspartic acid-N-monopropionic acid (ASMP-3Na) and 150 g of impurity salts (comprising 55 g of disodium aspartate, 31 g of disodium fumarate, 31 g of monosodium salt of β-alanine, 24 g of disodium iminodipropionate, 7 g of disodium malate and 2 g of sodium acrylate). The results are shown in Table 5.

EXAMPLE 88

An experiment was conducted in the same manner as in Example 85, except for using 1000 g of trisodium salt of (S)-α-alanine-N,N-diacetic acid (S-ALDA-3Na) and 200 g of impurity salts (comprising 100 g of monosodium salt of α-alanine, 40 g of monosodium salt of glycine, 30 g of disodium iminodiacetate and 30 g of trisodium nitrilotriacetate). The results are shown in Table 5.

EXAMPLE 89

An experiment was conducted in the same manner as in Example 85, except that the content of the impurity salts was 2.5% with the composition thereof being the same, the content of the compound of the formula [1] in the aqueous solution was 49.4%, and the aqueous solution was kept at 75° C. The results are shown in Table 5.

EXAMPLE 90

An experiment was conducted in the same manner as in Example 86, except that the content of the impurity salts was 2.0% with the composition thereof being the same, the content of the compound of the formula [1] in the aqueous solution was 49.5%, and the aqueous solution was kept at 75° C. The results are shown in Table 5.

EXAMPLE 91

An experiment was conducted in the same manner as in Example 87, except that the content of the impurity salts was 1.0% with the composition thereof being the same, the content of the compound of the formula [1] in the aqueous solution was 49.8%, and the aqueous solution was kept at 75° C. The results are shown in Table 5.

EXAMPLE 92

An experiment was conducted in the same manner as in Example 88, except that the content of the impurity salts was 1.2% with the composition thereof being the same, the content of the compound of the formula [1] in the aqueous solution was 49.5%, and the aqueous solution was kept at 75° C. The results are shown in Table 5.

EXAMPLE 93

An experiment was conducted in the same manner as in Example 85, except that the content of the impurity salts was 10.0% with the composition thereof being the same, the content of the compound of the formula [1] in the aqueous solution was 65.4%, and the aqueous solution was kept at 65° C. The results are shown in Table 5.

EXAMPLE 94

An experiment was conducted in the same manner as in Example 86, except that the content of the impurity salts was 10.0% with the composition thereof being the same, the content of the compound of the formula [1] in the aqueous solution was 65.4%, and the aqueous solution was kept at 65° C. The results are shown in Table 5.

EXAMPLE 95

An experiment was conducted in the same manner as in Example 87, except that the content of the impurity salts was 10.0% with the composition thereof being the same, the content of the compound of the formula [1] in the aqueous solution was 65.4%, and the aqueous solution was kept at 65° C. The results are shown in Table 5.

EXAMPLE 96

An experiment was conducted in the same manner as in Example 88, except that the content of the impurity salts was 10.0% with the composition thereof being the same, the content of the compound of the formula [1] in the aqueous solution was 65.4%, and the aqueous solution was kept at 65° C. The results are shown in Table 5.

EXAMPLE 97

An experiment was conducted in the same manner as in Example 85, except that the content of the impurity salts was 2.5% with the composition thereof being the same, the content of the compound of the formula [1] in the aqueous solution was 78.4%, and the aqueous solution was kept at 70° C. The results are shown in Table 5.

EXAMPLE 98

An experiment was conducted in the same manner as in Example 86, except that the content of the impurity salts was 2.0% with the composition thereof being the same, the content of the compound of the formula [1] in the aqueous solution was 78.7%, and the aqueous solution was kept at 70° C. The results are shown in Table 5.

EXAMPLE 99

An experiment was conducted in the same manner as in Example 87, except that the content of the impurity salts was 1.0% with the composition thereof being the same, the content of the compound of the formula [1] in the aqueous solution was 79.4%, and the aqueous solution was kept at 70° C. The results are shown in Table 5.

EXAMPLE 100

A dry powder comprising 1000 g of trisodium salt of taurine-N,N-diacetic acid (TUDA-3Na) and 250 g of impurity salts (comprising 50 g of monosodium salt of taurine, 50 g of disodium glycolate, 50 g of monosodium salt of glycine, 50 g of disodium iminodiacetate and 50 g of trisodium nitrilotriacetate) was dissolved in 1500 g of water in a stainless steel vessel externally provided with a thermoelectric heater to prepare a transparent aqueous solution with a light yellow color. This aqueous solution was kept at 50° C. for 60 days, and, then, the components were analyzed by HPLC and, simultaneously, the appearance of the solution was observed. The results are shown in Table 5.

EXAMPLE 101

An experiment was conducted in the same manner as in Example 100, except for using 1000 g of disodium N-methyliminodiacetate (MIDA-2Na) and 200 g of impurity salts (comprising 50 g of disodium glycolate, 50 g of monosodium salt of glycine, 50 g of disodium iminodiacetate and 50 g of trisodium nitrilotriacetate). The results are shown in Table 5.

EXAMPLE 102

An experiment was conducted in the same manner as in Example 100, except for using 1000 g of trisodium salt of anthranilic acid-N,N-diacetic acid (ANTDA-3Na) and 150 g of impurity salts (comprising 30 g of monosodium anthranilate, 60 g of disodium glycolate, 30 g of monosodium salt of glycine, 30 g of disodium iminodiacetate and 30 g of trisodium nitrilotriacetate). The results are shown in Table 5.

EXAMPLE 103

An experiment was conducted in the same manner as in Example 100, except that the content of the impurity salts was 2.5% with the composition thereof being the same, the content of the compound of the formula [1] in the aqueous solution was 49.4%, and the aqueous solution was kept at 75° C. The results are shown in Table 5.

EXAMPLE 104

An experiment was conducted in the same manner as in Example 101, except that the content of the impurity salts was 2.0% with the composition thereof being the same, the content of the compound of the formula [1] in the aqueous solution was 49.5%, and the aqueous solution was kept at 75° C. The results are shown in Table 5.

EXAMPLE 105

An experiment was conducted in the same manner as in Example 102, except that the content of the impurity salts was 1.0% with the composition thereof being the same, the content of the compound of the formula [1] in the aqueous solution was 49.8%, and the aqueous solution was kept at 75° C. The results are shown in Table 5.

EXAMPLE 106

An experiment was conducted in the same manner as in Example 100, except that the content of the impurity salts was 10.0% with the composition thereof being the same, the content of the compound of the formula [1] in the aqueous solution was 65.4%, and the aqueous solution was kept at 65° C. The results are shown in Table 5.

EXAMPLE 107

An experiment was conducted in the same manner as in Example 101, except that the content of the impurity salts was 10.0% with the composition thereof being the same, the content of the compound of the formula [1] in the aqueous solution was 65.4%, and the aqueous solution was kept at 65° C. The results are shown in Table 5.

EXAMPLE 108

An experiment was conducted in the same manner as in Example 102, except that the content of the impurity salts was 10.0% with the composition thereof being the same, the content of the compound of the formula [1] in the aqueous solution was 78.4%, and the aqueous solution was kept at 70° C. The results are shown in Table 5.

EXAMPLE 109

An experiment was conducted in the same manner as in Example 101, except that the content of the impurity salts was 2.0% with the composition thereof being the same, the content of the compound of the formula [1] in the aqueous solution was 78.7%, and the aqueous solution was kept at 70° C. The results are shown in Table 5.

EXAMPLE 110

An experiment was conducted in the same manner as in Example 100, except that 1000 g of iron salt of anthranilic acid-N,N-diacetic acid (ANTDA-Fe) and 20 g of impurity Fe salts (comprising 4 g of anthranilate, 8 g of glycolate, 4 g of glycine salt, 4 g of iminodiacetate and 4 g of nitrilotriacetate) were used, the content of the compound of the formula [1] in the aqueous solution was 49.5%, and the aqueous solution was kept at 40° C. The results are shown in Table 5.

EXAMPLE 111

An experiment was conducted in the same manner as in Example 100, except that 1000 g of iron salt of anthranilic acid-N,N-diacetic acid (ANTDA-Fe) and 10 g of impurity Fe salts (comprising 2 g of anthranilate, 4 g of glycolate, 2 g of glycine salt, 2 g of iminodiacetate and 2 g of nitrilotriacetate) were used, the content of the compound of the formula [1] in the aqueous solution was 39.8%, and the aqueous solution was kept at 40° C. The results are shown in Table 5.

COMPARATIVE EXAMPLE 29

An experiment was conducted in the same manner as in Example 85, except that the content of the impurity salts was 35.0% with the composition thereof being the same, the content of the compound of the formula [1] in the aqueous solution was 35.1%, and the aqueous solution was kept at 50° C. The results are shown in Table 6.

COMPARATIVE EXAMPLE 30

An experiment was conducted in the same manner as in Example 86, except that the content of the impurity salts was 35.0% with the composition thereof being the same, the content of the compound of the formula [1] in the aqueous solution was 35.1%, and the aqueous solution was kept at 50° C. The results are shown in Table 6.

COMPARATIVE EXAMPLE 31

An experiment was conducted in the same manner as in Example 87, except that the content of the impurity salts was 35.0% with the composition thereof being the same, the content of the compound of the formula [1] in the aqueous solution was 35.1%, and the aqueous solution was kept at 50° C. The results are shown in Table 6.

COMPARATIVE EXAMPLE 32

An experiment was conducted in the same manner as in Example 88, except that the content of the impurity salts was 35.0% with the composition thereof being the same, the content of the compound of the formula [1] in the aqueous solution was 35.1%, and the aqueous solution was kept at 50° C. The results are shown in Table 6.

COMPARATIVE EXAMPLE 33

An experiment was conducted in the same manner as in Example 85, except that the content of the impurity salts was 50.0% with the composition thereof being the same, the content of the compound of the formula [1] in the aqueous solution was 33.3%, and the aqueous solution was kept at 50° C. The results are shown in Table 6.

COMPARATIVE EXAMPLE 34

An experiment was conducted in the same manner as in Example 85, except that the content of the impurity salts was 35.0% with the composition thereof being the same, the content of the compound of the formula [1] in the aqueous solution was 35.1%, and the aqueous solution was kept at 75° C. The results are shown in Table 6.

COMPARATIVE EXAMPLE 35

An experiment was conducted in the same manner as in Example 85, except that the content of the impurity salts was 28.0% with the composition thereof being the same, the content of the compound of the formula [1] in the aqueous solution was 51.4%, and the aqueous solution was kept at 60° C. The results are shown in Table 6.

COMPARATIVE EXAMPLE 36

An experiment was conducted in the same manner as in Example 86, except that the content of the impurity salts was 35.0% with the composition thereof being the same, the content of the compound of the formula [1] in the aqueous solution was 35.1%, and the aqueous solution was kept at 50° C. The results are shown in Table 6.

COMPARATIVE EXAMPLE 37

An experiment was conducted in the same manner as in Example 100, except that the content of the impurity salts was 35.0% with the composition thereof being the same, the content of the compound of the formula [1] in the aqueous solution was 35.1%, and the aqueous solution was kept at 50° C. The results are shown in Table 6.

COMPARATIVE EXAMPLE 38

An experiment was conducted in the same manner as in Example 101, except that the content of the impurity salts was 35.0% with the composition thereof being the same, the content of the compound of the formula [1] in the aqueous solution was 35.1%, and the aqueous solution was kept at 50° C. The results are shown in Table 6.

COMPARATIVE EXAMPLE 39

An experiment was conducted in the same manner as in Example 102, except that the content of the impurity salts was 35.0% with the composition thereof being the same, the content of the compound of the formula [1] in the aqueous solution was 35.1%, and the aqueous solution was kept at 50° C. The results are shown in Table 6.

COMPARATIVE EXAMPLE 40

An experiment was conducted in the same manner as in Example 100, except that the content of the impurity salts was 50.0% with the composition thereof being the same, the content of the compound of the formula [1] in the aqueous solution was 33.3%, and the aqueous solution was kept at 50° C. The results are shown in Table 6.

COMPARATIVE EXAMPLE 41

An experiment was conducted in the same manner as in Example 101, except that the content of the impurity salts was 35.0% with the composition thereof being the same, the content of the compound of the formula [1] in the aqueous solution was 35.1%, and the aqueous solution was kept at 75° C. The results are shown in Table 6.

COMPARATIVE EXAMPLE 42

An experiment was conducted in the same manner as in Example 110, except that the content of the impurity salts was 28.0% with the composition thereof being the same, the content of the compound of the formula [1] in the aqueous solution was 43.8%, and the aqueous solution was kept at 40° C. The results are shown in Table 6.

TABLE 5

| Example | Compound of the formula [I] | Content* of impurity wt. % | Keeping temperature ° C. | Change before and after kept for 60 days** wt. % | Appearance |
|---|---|---|---|---|---|
| 85 | S-ASMA-3Na | 25.0 | 50 | 36.4<br>↓<br>35.4 | Light yellow transparent aqueous solution<br>↓<br>Light yellow transparent aqueous solution |
| 86 | S-ASDA-4Na | 20.0 | 50 | 37.0<br>↓<br>36.4 | Light yellow transparent aqueous solution<br>↓<br>Light yellow transparent aqueous solution |
| 87 | S-ASMP-3Na | 15.0 | 50 | 37.8<br>↓<br>37.8 | Light yellow transparent aqueous solution<br>↓<br>Light yellow transparent aqueous solution |
| 88 | S-ALDA-3Na | 20.0 | 50 | 37.0<br>↓<br>36.5 | Light yellow transparent aqueous solution<br>↓<br>Light yellow transparent aqueous solution |
| 89 | S-ASMA-3Na | 2.5 | 75 | 49.4<br>↓<br>49.4 | Colorless transparent aqueous solution<br>↓<br>Colorless transparent aqueous solution |
| 90 | S-ASDA-4Na | 2.0 | 75 | 49.5<br>↓<br>49.5 | Colorless transparent aqueous solution<br>↓<br>Colorless transparent aqueous solution |
| 91 | S-ASMP-3Na | 1.0 | 75 | 49.8<br>↓<br>49.8 | Colorless transparent aqueous solution<br>↓<br>Colorless transparent aqueous solution |
| 92 | S-ALDA-3Na | 1.0 | 75 | 49.8<br>↓<br>49.8 | Colorless transparent aqueous solution<br>↓<br>Colorless transparent aqueous solution |
| 93 | S-ASMA-3Na | 10.0 | 65 | 65.4<br>↓<br>63.7 | Light yellow slurry<br>↓<br>Light yellow slurry |
| 94 | S-ASDA-4Na | 10.0 | 65 | 65.4<br>↓<br>64.5 | Light yellow slurry<br>↓<br>Light yellow slurry |
| 95 | S-ASMP-3Na | 10.0 | 65 | 65.4<br>↓<br>65.4 | Light yellow slurry<br>↓<br>Light yellow slurry |
| 96 | S-ALDA-3Na | 10.0 | 65 | 65.4<br>↓<br>64.7 | Light yellow slurry<br>↓<br>Light yellow slurry |
| 97 | S-ASMA-3Na | 2.5 | 70 | 78.4<br>↓<br>76.8 | White slurry<br>↓<br>White slurry |

TABLE 5-continued

| Example | Compound of the formula [I] | Content* of impurity wt. % | Keeping temperature ° C. | Change before and after kept for 60 days** wt. % | Appearance |
|---|---|---|---|---|---|
| 98 | S-ASDA-4Na | 2.0 | 70 | 78.7 ↓ 78.5 | White slurry ↓ White slurry |
| 99 | S-ASMP-3Na | 1.0 | 70 | 79.4 ↓ 79.4 | White slurry ↓ White slurry |
| 100 | TUDA-3Na | 25.0 | 50 | 36.4 ↓ 34.7 | Light yellow transparent aqueous solution ↓ Light yellow transparent aqueous solution |
| 101 | MIDA-2Na | 20.0 | 50 | 37.0 ↓ 36.6 | Light yellow transparent aqueous solution ↓ Light yellow transparent aqueous solution |
| 102 | ANTDA-3Na | 15.0 | 50 | 37.8 ↓ 37.8 | Light yellow transparent aqueous solution ↓ Light yellow transparent aqueous solution |
| 103 | TUDA-3Na | 2.5 | 75 | 49.4 ↓ 49.4 | Colorless transparent aqueous solution ↓ Colorless transparent aqueous solution |
| 104 | MIDA-2Na | 2.0 | 75 | 49.5 ↓ 49e5 | Colorless transparent aqueous solution ↓ Colorless transparent aqueous solution |
| 105 | ANTDA-3Na | 1.0 | 75 | 49.8 ↓ 49.8 | Colorless transparent aqueous solution ↓ Colorless transparent aqueous solution |
| 106 | TUDA-3Na | 10.0 | 65 | 65.4 ↓ 63.7 | Light yellow slurry ↓ Light yellow slurry |
| 107 | MIDA-2Na | 10.0 | 65 | 65.4 ↓ 64.5 | Light yellow slurry ↓ Light yellow slurry |
| 108 | TUDA-3Na | 2.5 | 70 | 78.4 ↓ 76.9 | White slurry ↓ White slurry |
| 109 | MIDA-2Na | 2.0 | 70 | 78.7 ↓ 78.5 | White slurry ↓ White slurry |
| 110 | ANTDA-Fe | 2.0 | 40 | 49.5 ↓ 49.3 | Reddish brown aqueous solution ↓ Reddish brown aqueous solution |
| 111 | ANTDA-Fe | 1.0 | 40 | 39.8 ↓ 39.8 | Reddish brown aqueous solution ↓ Reddish brown aqueous solution |

$$^{*}(\text{Content of impurity}) = \frac{(\text{Weight of impurity})}{(\text{Weight of the compound of the formula [I]})} \times 100 \ [\text{wt. \%}]$$

**wt. %: Content of the compound of the formula [I] in aqueous solution
The upper row: Before kept at the given temperature for 60 days (just after preparation of the aqueous solution)
The lower row: After kept for 60 days

TABLE 6

| Comparative Example | Compound of the formula [I] | Content* of impurity wt. % | Keeping temperature ° C. | Change before and after kept for 60 days** wt. % | Appearance |
|---|---|---|---|---|---|
| 29 | S-ASMA-3Na | 35.0 | 50 | 35.1 | Light yellow transparent aqueous solution |
| 29 | S-ASMA-3Na | 35.0 | 50 | 35.1 ↓ 31.1 | Light yellow transparent aqueous solution ↓ Brown aqueous solution |
| 30 | S-ASDA-4Na | 35.0 | 50 | 35.1 ↓ 31.8 | Light yellow transparent aqueous solution ↓ Brown aqueous solution |
| 31 | S-ASMP-3Na | 35.0 | 50 | 33.3 ↓ 33.2 | Light yellow transparent aqueous solution ↓ Brown aqueous solution |
| 32 | S-ALDA-3Na | 35.0 | 50 | 35.1 ↓ 31.8 | Light yellow transparent aqueous solution ↓ Brown aqueous solution |

TABLE 6-continued

| Comparative Example | Compound of the formula [I] | Content* of impurity wt. % | Keeping temperature ° C. | Change before and after kept for 60 days** wt. % | Appearance |
|---|---|---|---|---|---|
| 33 | S-ASMA-3Na | 50.0 | 50 | 33.3 ↓ 30.5 | Light yellow transparent slurry ↓ Brown slurry |
| 34 | S-ASMA-4Na | 35.0 | 75 | 35.1 ↓ 30.6 | Light yellow transparent aqueous solution ↓ Brown aquequs solution |
| 35 | S-ASMA-3Na | 28.0 | 60 | 51.4 ↓ 47.3 | Light yellow transparent slurry ↓ Brown slurry |
| 36 | S-ASDA-4Na | 28.0 | 60 | 51.4 ↓ 48.3 | Light yellow transparent slurry ↓ Brown slurry |
| 37 | TUDA-3N | 35.0 | 50 | 35.1 ↓ 30.4 | Light yellow transparent aqueous solution ↓ Brown aqueous solution |
| 38 | MIDA-2Na | 35.0 | 50 | 35.1 ↓ 29.9 | Light yellow transparent aqueous solution ↓ Brown aqueous solution |
| 39 | ANTDA-3Na | 35.0 | 50 | 35.1 ↓ 31.8 | Light yellow transparent aqueous solution ↓ Brown aqueous solution |
| 40 | TUDA-3Na | 50.0 | 5 | 33.3 ↓ 29.5 | Light yellow transparent slurry ↓ Brown slurry |
| 41 | MIDA-2Na | 35.0 | 75 | 35.1 ↓ 29.6 | Light yellow transparent aqueous solution ↓ Light yellow transparent aqueous solution |
| 42 | ANTDA-Fe | 28.0 | 40 | 43.8 ↓ 40.6 | Reddish brown aqueous solution ↓ Blackish brown aqueous solution |

$$^{*}\ (\text{Content of impurity}) = \frac{(\text{Weight of impurity})}{(\text{Weight of the compound of the formula [I]})} \times 100\ [\text{wt. \%}]$$

**wt. %: Content of the compound of the formula [I] in aqueous solution
The upper row: Before kept at the given temperature for 60 days (just after preparation of the aqueous solution)
The lower row: After kept for 60 days

EXAMPLE 112

A dry powder comprising 1000 g of tetrasodium ethylenediamine-N,N'-disuccinate (EDDS-4Na) and 250 g of impurity salts (comprising 100 g of disodium maleate, 100 g of disodium fumarate and 50 g of disodium ethylenediaminemonosuccinate) was dissolved in 1500 g of water in a stainless steel vessel externally provided with a thermoelectric heater to prepare a transparent aqueous solution with a light yellow color. This aqueous solution was kept at 50° C. for 60 days. Then, the components were analyzed by HPLC and, simultaneously, the appearance of the solution was observed. The results are shown in Table 7.

EXAMPLE 113

An experiment was conducted in the same manner as in Example 112, except for using 1000 g of tetrasodium (S,S)-ethylenediamine-N,N'-disuccinate (SS-EDDS-4Na) and 200 g of impurity salts (comprising 40 g of disodium (S)-aspartate, 40 g of disodium (S)-N-(2-chloroethyl)-aspartate, 40 g of disodium (S)-N-(2-hydroxyethyl)-aspartate, 40 g tetrasodium of (S,S)-N-(2-hydroxyethyl)-ethylenediamine-N,N'-disuccinate and 40 g of disodium fumarate). The results are shown in Table 7.

EXAMPLE 114

An experiment was conducted in the same manner as in Example 112, except for using a dry powder comprising 1000 g of tetrasodium 1,3-propanediamine-N,N'-disuccinate (PDDS-4Na) and 250 g of impurity salts (comprising 100 g of disodium maleate, 100 g of disodium fumarate and 50 g of disodium ethylenediaminemonosuccinate). The results are shown in Table 7.

EXAMPLE 115

An experiment was conducted in the same manner as in Example 112, except for using 1000 g of tetrasodium (S,S)-1,3-propanediamine-N,N'-disuccinate (SS-PDDS-4Na) and 200 g of impurity salts (comprising 40 g of disodium (S)-aspartate, 40 g of disodium (S)-N-(2-chloropropyl)-aspartate, 40 g of disodium (S)-2-hydroxypropylaspartate, 40 g of tetrasodium (S,S)-N-(2-hydroxypropyl)-1,3-propanediamine-N,N'-disuccinate and 40 g of disodium fumarate). The results are shown in Table 7.

EXAMPLE 116

An experiment was conducted in the same manner as in Example 112, except for using 1000 g of tetrasodium (S,S)-2-hydroxy-1,3-propanediamine-N,N'-disuccinate (SS-PDDS-OH-4Na) and 150 g of impurity salts (comprising 50 g of disodium (S)-aspartate, 50 g of disodium (S)-N-(1,2-dihydroxypropyl)-aspartate and 50 g of disodium fumarate). The results are shown in Table 7.

EXAMPLE 117

An experiment was conducted in the same manner as in Example 112, except that the content of the impurity salts was 1.0% with the composition thereof being the same, the content of the compound of the formula [1] in the aqueous solution was 49.8%, and the aqueous solution was kept at 75° C. The results are shown in Table 7.

EXAMPLE 118

An experiment was conducted in the same manner as in Example 113, except that the content of the impurity salts was 10.0% with the composition thereof being the same, the content of the compound of the formula [1] in the slurry solution was 65.4%, and the solution was kept at 65° C. The results are shown in Table 7.

EXAMPLE 119

An experiment was conducted in the same manner as in Example 114, except that the content of the impurity salts was 10.0% with the composition thereof being the same, the content of the compound of the formula [1] in the slurry solution was 65.4%, and the solution was kept at 65° C. The results are shown in Table 7.

EXAMPLE 120

An experiment was conducted in the same manner as in Example 115, except that the content of the impurity salts was 2.5% with the composition thereof being the same, the content of the compound of the formula [1] in the slurry solution was 78.4%, and the solution was kept at 70° C. The results are shown in Table 7.

EXAMPLE 121

An experiment was conducted in the same manner as in Example 116, except that the content of the impurity salts was 2.0% with the composition thereof being the same, the content of the compound of the formula [1] in the slurry solution was 78.7%, and the solution was kept at 70° C. The results are shown in Table 7.

EXAMPLE 122

An experiment was conducted in the same manner as in Example 112, except that the content of the impurity salts was 10.0% with the composition thereof being the same, the content of the compound of the formula [1] in the aqueous solution was 74.1%, and the solution was kept at 40° C. The results are shown in Table 7.

EXAMPLE 123

An experiment was conducted in the same manner as in Example 114, except that the content of the impurity salts was 10.0% with the composition thereof being the same, the content of the compound of the formula [1] in the slurry solution was 74.1%, and the solution was kept at 40° C. The results are shown in Table 7.

EXAMPLE 124

A dry powder comprising 1000 g of copper disodium ethylenediamine-N,N'-disuccinate (EDDS-Cu-2Na) and 250 g of impurity salts (comprising 100 g of disodium maleate, 100 g of disodium fumarate and 50 g of disodium ethylenediaminemonosuccinate) was dissolved in 1500 g of water in a stainless steel vessel externally provided with a thermoelectric heater to prepare a transparent aqueous solution with a light yellow color. This aqueous solution was kept at 50° C. for 60 days. Then, the components were analyzed by HPLC and, simultaneously, the appearance of the solution was observed. The results are shown in Table 7.

EXAMPLE 125

An experiment was conducted in the same manner as in Example 112, except for using 1000 g of iron ammonium (S,S)-ethylenediamine-N,N'-disuccinate (SS-EDDS-Fe—NH4) and 200 g of impurity salts (comprising 40 g of diammonium (S)-aspartate, 40 g of diammonium (S)-N-(2-chloroethyl)-aspartate, 40 g of diammonium (S)-N-(2-hydroxyethyl)-aspartate, 40 g of tetraammonium (S,S)-N-(2-hydroxyethyl)-ethylenediamine-N,N'-disuccinate and 40 g of diammonium fumarate). The results are shown in Table 7.

EXAMPLE 126

An experiment was conducted in the same manner as in Example 112, except for using a dry powder comprising 1000 g of copper disodium 1,3-propanediamine-N,N'-disuccinate (PDDS-Cu-2Na) and 250 g of impurity salts (comprising 100 g of disodium maleate, 100 g of disodium fumarate and 50 g of disodium ethylenediaminemonosuccinate). The results are shown in Table 7.

EXAMPLE 127

An experiment was conducted in the same manner as in Example 112, except for using 1000 g of nickel disodium (S,S)-1,3-propanediamine-N,N'-disuccinate (SS-PDDS-Ni-2Na) and 200 g of impurity salts (comprising 40 g of disodium (S)-aspartate, 40 g of disodium (S)-N-(2-chloropropyl)-aspartate, 40 g of disodium (S)-2-hydroxypropylaspartate, 40 g of tetrasodium (S,S)-N-(2-hydroxypropyl)-1,3-propanediamine-N,N'-disuccinate and 40 g of disodium fumarate). The results are shown in Table 7.

EXAMPLE 128

An experiment was conducted in the same manner as in Example 112, except for using 1000 g of copper disodium (S,S)-2-hydroxy-1,3-propanediamine-N,N'-disuccinate (SS-PDDS-Cu-2Na) and 150 g of impurity salts (comprising 50 g of disodium (S)-aspartate, 50 g of disodium (S)-N-(1,2-dihydroxypropyl)-aspartate and 50 g of disodium fumarate). The results are shown in Table 7.

COMPARATIVE EXAMPLE 43

An experiment was conducted in the same manner as in Example 112, except that the content of the impurity salts was 30.0% with the composition thereof being the same, the content of the compound of the formula [1] in the aqueous solution was 35.7%, and the aqueous solution was kept at 50° C. The results are shown in Table 8.

COMPARATIVE EXAMPLE 44

An experiment was conducted in the same manner as in Example 113, except that the content of the impurity salts was 30.0% with the composition thereof being the same, the content of the compound of the formula [1] in the aqueous solution was 35.7%, and the aqueous solution was kept at 50° C. The results are shown in Table 8.

COMPARATIVE EXAMPLE 45

An experiment was conducted in the same manner as in Example 114, except that the content of the impurity salts was 50.0% with the composition thereof being the same, the content of the compound of the formula [1] in the aqueous solution was 33.3%, and the aqueous solution was kept at 50° C. The results are shown in Table 8.

COMPARATIVE EXAMPLE 46

An experiment was conducted in the same manner as in Example 115, except that the content of the impurity salts was 40.0% with the composition thereof being the same, the content of the compound of the formula [1] in the aqueous solution was 41.6%, and the aqueous solution was kept at 75° C. The results are shown in Table 8.

COMPARATIVE EXAMPLE 47

An experiment was conducted in the same manner as in Example 116, except that the content of the impurity salts was 30.0% with the composition thereof being the same, the content of the compound of the formula [1] in the aqueous solution was 43.5%, and the aqueous solution was kept at 75° C. The results are shown in Table 8.

COMPARATIVE EXAMPLE 48

An experiment was conducted in the same manner as in Example 124, except that the content of the impurity salts was 30.0% with the composition thereof being the same, the content of the compound of the formula [1] in the aqueous solution was 35.7%, and the aqueous solution was kept at 50° C. The results are shown in Table 8.

COMPARATIVE EXAMPLE 49

An experiment was conducted in the same manner as in Example 125, except that the content of the impurity salts was 30.0% with the composition thereof being the same, the content of the compound of the formula [1] in the aqueous solution was 35.7%, and the aqueous solution was kept at 50° C. The results are shown in Table 8.

COMPARATIVE EXAMPLE 50

An experiment was conducted in the same manner as in Example 126, except that the content of the impurity salts was 30.0% with the composition thereof being the same, the content of the compound of the formula [1] in the aqueous solution was 35.7%, and the aqueous solution was kept at 50° C. The results are shown in Table 8.

COMPARATIVE EXAMPLE 51

An experiment was conducted in the same manner as in Example 127, except that the content of the impurity salts was 30.0% with the composition thereof being the same, the content of the compound of the formula [1] in the aqueous solution was 43.5%, and the aqueous solution was kept at 75° C. The results are shown in Table 8.

COMPARATIVE EXAMPLE 52

An experiment was conducted in the same manner as in Example 128, except that the content of the impurity salts was 30.0% with the composition thereof being the same, the content of the compound of the formula [1] in the aqueous solution was 43.5%, and the aqueous solution was kept at 75° C. The results are shown in Table 8.

It has become clear from these examples that when the impurity salts are present in a large amount for the compound of the formula [1] in the aqueous solution or slurry, deterioration of purity and coloration due to the decomposition of the compound of the formula [1] proceed during storage.

According to the present invention, the compounds of the formula [1] which have been considerably difficult to handle in the form of solid can be stored or handled as an aqueous solution or slurry stably for a long period of time without causing deterioration in purity or coloration due to decomposition of the components by reducing the content of the coexisting impurity salts and setting a proper water content or a proper temperature at which the aqueous solution or slurry is kept.

TABLE 7

| Example | Compound of the formula [I] | Content* of impurity wt. % | Keeping temperature ° C. | Change before and after kept at the given temperature for 60 days** wt. % | Appearance |
|---|---|---|---|---|---|
| 112 | EDDS-4Na | 25.0 | 50 | 36.4 ↓ 36.4 | Light yellow transparent aqueous solution ↓ Light yellow transparent aqueous solution |
| 113 | SS-EDDS-4Na | 20.0 | 50 | 37.0 ↓ 35.6 | Light yellow transparent aqueous solution ↓ Light yellow transparent aqueous solution |
| 114 | PDDS-4Na | 25.0 | 50 | 36.4 ↓ 36.4 | Light yellow transparent aqueous solution ↓ Light yellow transparent aqueous solution |
| 115 | SS-PDDS-4Na | 20.0 | 75 | 45.4 ↓ 44.3 | Colorless transparent aqueous solution ↓ Colorless transparent aqueous solution |
| 116 | SS-OPDDS-4Na | 15.0 | 75 | 46.5 ↓ 44.7 | Colorless transparent aqueous solution ↓ Colorless transparent aqueous solution |
| 117 | EDDS-4Na | 1.0 | 75 | 49.8 ↓ 49.8 | Colorless transparent aqueous solution ↓ Colorless transparent aqueous solution |
| 118 | SS-EDDS-4Na | 10.0 | 65 | 65.4 ↓ 65.4 | Light yellow slurry ↓ Light yellow slurry |

TABLE 7-continued

| Example | Compound of the formula [I] | Content* of impurity wt. % | Keeping temperature ° C. | Change before and after kept at the given temperature for 60 days** wt. % | Appearance |
|---|---|---|---|---|---|
| 119 | PDDS-4Na | 10.0 | 65 | 65.4<br>↓<br>65.4 | Light yellow slurry<br>↓<br>Light yellow slurry |
| 120 | SS-PDDS-4Na | 2.5 | 70 | 78.4<br>↓<br>78.4 | White slurry<br>↓<br>White slurry |
| 121 | SS-OPDDS-4Na | 2.0 | 70 | 78.7<br>↓<br>78.7 | White slurry<br>↓<br>White slurry |
| 122 | EDDS-4Na | 10.0 | 40 | 74.1<br>↓<br>74.1 | White slurry<br>↓<br>White slurry |
| 123 | PDDS-4Na | 10.0 | 40 | 74.1<br>↓<br>74.1 | White slurry<br>↓<br>White slurry |
| 124 | EDDS-Cu-2Na | 25.0 | 50 | 36.4<br>↓<br>36.3 | Dark blue transparent aqueous solution<br>↓<br>Dark blue transparent aqueous solution |
| 125 | SS-EDDS-Fe-$NH_4$ | 20.0 | 50 | 37.0<br>↓<br>36.5 | Reddish brown aqueous solution<br>↓<br>Reddish brown aqueous solution |
| 126 | PDDS-Cu-2Na | 25.0 | 50 | 36.4<br>↓<br>36.4 | Dark blue transparent aqueous solution<br>↓<br>Dark blue transparent aqueous solution |
| 127 | SS-PDDS-Ni-2Na | 20.0 | 75 | 45.4<br>↓<br>44.0 | Blue transparent aqueous solution<br>↓<br>Blue transparent aqueous solution |
| 128 | SS-PDDS-OH-Cu-2Na | 15.0 | 75 | 49.4<br>↓<br>47.9 | Dark blue transparent aqueous solution<br>↓<br>Dark blue transparent aqueous solution |

$$^{*}\ (\text{Content of impurity}) = \frac{(\text{Weight of impurity})}{(\text{Weight of the compound of the formula [I]})} \times 100\ [\text{wt. }\%]$$

**wt. %: Content of the compound of the formula [I] in aqueous solution
The upper row: Before kept at the given temperature for 60 days (just after preparation of the aqueous solution)
The lower row: After kept at the given temperature for 60 days

TABLE 8

| Comparative Example | Compound of the formula [I] | Content* of impurity wt. % | Keeping temperature ° C. | Change before and after kept at the given temperature for 60 days** wt. % | Appearance |
|---|---|---|---|---|---|
| 43 | EDDS-4Na | 30.0 | 50 | 35.7<br>↓<br>35.7 | Light yellow transparent aqueous solution<br>↓<br>Light yellow transparent aqueous solution |
| 44 | SS-EDDS-4Na | 30.0 | 50 | 35.7<br>↓<br>34.4 | Light yellow transparent aqueous solution<br>↓<br>Light yellow transparent aqueous solution |
| 45 | PDDS-4Na | 50.0 | 50 | 33.3<br>↓<br>33.3 | Light yellow transparent aqueous solution<br>↓<br>Light yellow transparent aqueous solution |
| 46 | SS-PDDS-4Na | 40.0 | 75 | 41.6<br>↓<br>40.7 | Colorless transparent aqueous solution<br>↓<br>Colorless transparent aqueous solution |
| 47 | SS-PDDS-OH-4Na | 30.0 | 75 | 43.5<br>↓<br>41.8 | Colorless transparent aqueous solution<br>↓<br>Colorless transparent aqueous solution |
| 48 | EDDS-Cu-2Na | 30.0 | 50 | 35.7<br>↓<br>31.4 | Dark blue transparent aqueous solution<br>↓<br>Dark blue transparent aqueous solution |
| 49 | SS-EDDS-Fe-$NH_4$ | 30.0 | 50 | 5.7<br>↓<br>29.9 | Reddish brown aqueous solution<br>↓<br>Blackish brown aqueous solution |
| 50 | PDDS-Cu-2Na | 30.0 | 50 | 35.7<br>↓<br>32.2 | Dark blue transparent aqueous solution<br>↓<br>Dark blue transparent aqueous solution |

TABLE 8-continued

| Comparative Example | Compound of the formula [I] | Content* of impurity wt. % | Keeping temperature ° C. | Change before and after kept at the given temperature for 60 days** wt. % | Appearance |
|---|---|---|---|---|---|
| 51 | SS-PDDS-Ni-2Na | 30.0 | 75 | 43.5 ↓ 38.4 | Blue transparent aqueous solution ↓ Blue transparent aqueous solution |
| 52 | SS-PDDS-OH-Cu-2Na | 30. 0 | 75 | 43.5 ↓ 38.7 | Dark blue transparent aqueous solution ↓ Dark blue transparent aqueous solution |

$$* \quad \text{(Content of impurity)} = \frac{\text{(Weight of impurity)}}{\text{(Weight of the compound of the formula [I])}} \times 100 \quad \text{[wt. \%]}$$

**wt. %: Content of the compound of the formula [I] in aqueous solution
The upper row: Before kept at the given temperature for 60 days (just after preparation of the aqueous solution)
The lower row: After kept at the given temperature for 60 days

Detergent Composition

Method for the Measurement of Detergency

1) Preparation of Artificial Soil

A clay mainly composed of kaolinite, vermiculite or the like which is a crystalline mineral was dried at 200° C. for 30 hours, and this was used as an inorganic soil.

3.5 Grams of gelatin was dissolved in 950 cc of water at about 40° C., and, then, 0.25 g of carbon black was dispersed in water by an emulsification dispersing machine. Then, 14.9 g of the inorganic soil was added and emulsified and, furthermore, 31.35 g of the organic soil was added thereto and emulsified and dispersed to prepare a stable soil bath. A given cleaning cloth (cotton cloth #60 designated by Japan Oil Chemical Society) of 10 cm×20 cm was dipped in the soil bath and, thereafter, squeezed by twin rubber roll made of rubber to remove water and the adhesion amount of the soil was made uniform, followed by subjecting both sides of the cloth to rubbing 25 times each. The cloth was cut to 5 cm×5 cm and those of 42±2% in reflectance were used as soiled cloths. The composition of the soils of the resulting artificial soiled cloths is as shown in Table 9.

TABLE 9

| Soil components | Composition (wt %) |
|---|---|
| Organic soil | |
| Oleic acid | 28.3 |
| Triolein | 15.6 |
| Cholesterol oleate | 12.2 |
| Liquid paraffin | 2.5 |
| Squalene | 2.5 |
| Cholesterol | 1.6 |
| Total of oily soils | 62.7 |
| Gelatin | 7.0 |
| Inorganic soil | 29.8 |
| Carbon black (designated by Japan Oil Chemical Society) | 0.5 |

2) Method of Cleaning

Ten artificially soiled cloths and knitted cloths were introduced into Terg-O-Tometer manufactured by Testing Co., Ltd. U.S. and with setting the bath ratio to 30 times, cleaning was carried out at 120 rpm and at 25° C. for 10 minutes. A cleaning solution of 0.083% in detergent concentration was used in an amount of 900 ml, and rinsing was carried out with 900 ml of water for 3 minutes. Water of 3°DH was used.

3) Evaluation

Detergency was obtained by the formula (5).

$$\text{Detergency (\%)} = \frac{(K/S \text{ of soiled cloth} - K/S \text{ of cleaned cloth})}{(K/S \text{ of soiled cloth} - K/S \text{ of unsoiled cloth})} \times 100 \quad (5)$$

$K/S=(1-R/100)/(2R/100)$

R denotes the reflectance (%) measured by a reflectometer. The detergency was evaluated in terms of the average value of the results on the ten artificially soiled cloths tested.

EXAMPLE 129

A detergent slurry of 60% in solid content was prepared using the components of the detergent compositions shown in Tables 10–21 given hereinafter from which the nonionic surface active agent, a part of the silicate, a part of sodium carbonate, the enzyme and the perfume were excluded. The detergent slurry was dried using a counter-current spray drying tower at a hot air temperature of 270° C. so that water content reached 5%, thereby to obtain a spray dried product.

This spray dried product, a nonionic surface active agent and water were introduced into a continuous kneader to obtain a dense and uniform kneaded product. A porous plate (10 mm thick) having 80 holes of 5 mmφ (diameter) was provided at the outlet of the kneader and the kneaded product was made to cylindrical pellets of about 5 mmφ×10 mm.

The pellets were introduced together with cooling air of 15° C. in an amount twice (by weight) that of the pellets into a crusher. The crusher had cutters of 15 cm long at crossing four stages, which revolve at 3000 rpm, and screen comprises a punching metal of 3600, with diameter of the holes being 20 mmφ and the opening being 20%.

The particles which passed through the screen were mixed with taurine-N,N-diacetic acid derivative powder, 6.5% by weight of pulverized sodium carbonate and 2% by weight of silicate powder, and thereto were added the enzyme and the perfume to obtain a detergent composition having the composition as shown in Tables 10–21 given hereinafter. The detergency of the detergent composition was evaluated.

The meaning and detail of the abbreviations in Tables 10–21 are as follows. EOp indicates the average addition mol number of ethylene oxide and POp indicates the average addition mol number of propylene oxide.

(1) Anionic surface active agents:

α-SF: Sodium salt of α-sulfofatty acid ($C_{14}$–$C_{16}$) methyl ester.

AOS: Sodium α-olefinsulfonates ($C_{14}$–$C_{18}$).

LAS: Sodium alkylbenzenesulfonate (alkyl group: $C_{10}$–$C_{14}$).

(2) Nonionic surface active agents:

AE: $C_{12}$ alcohol ethoxylate (EOp=15).

NFE: Nonylphenol ethoxylate (EOp=15).

AOE.PO: EO.PO adducts of $C_{12}$–$C_{13}$ alcohols (EOp=15, POp=5).

FEE: $C_{11}H_{23}CO(OCH_2OCH_2)_{15}OCH_3$ (3) Builders:

TUDA: Trisodium salt of taurine-N,N-diacetic acid

Silicates: A type zeolite (4) Enzymes: protease, amylase, cellulase, lipase (5) Other additives:

Fluorescent agent

Perfume

PAa: Sodium polyacrylate

PEG400: Polyethylene glycol #400

TABLE 10

| Sample No. | 1 | 2 | 3 | 4 | 5 | 6 | 7 | 8 |
|---|---|---|---|---|---|---|---|---|
| Composition (wt. %) | | | | | | | | |
| Anionic: | | | | | | | | |
| α-SF | 20 | 20 | 20 | 20 | 20 | 20 | 20 | 20 |
| AOS | 3 | 3 | 5 | — | 3 | 3 | 3 | 3 |
| LAS | 2 | 2 | — | 5 | 2 | 2 | 2 | 2 |
| Nonionic: | | | | | | | | |
| AE | 5 | 5 | 5 | 5 | 5 | — | — | — |
| NFE | 3 | 3 | 3 | 3 | — | 5 | — | — |
| AOE.PO | 2 | 2 | 2 | 2 | — | — | 5 | — |
| FEE | — | — | — | — | — | — | — | 5 |
| Builders: | | | | | | | | |
| ASDA | 5 | 10 | 10 | 10 | 10 | 10 | 10 | 10 |
| Potassium carbonate | 8 | 8 | 8 | 8 | 8 | 8 | 8 | 8 |
| Sodium carbonate | 22 | 22 | 22 | 22 | 22 | 22 | 22 | 22 |
| Enzymes: | | | | | | | | |
| Protease | 0.5 | 0.5 | 0.5 | 0.5 | 0.5 | 0.5 | 0.5 | 0.5 |
| Amylase | 0.1 | 0.1 | 0.1 | 0.1 | 0.1 | 0.1 | 0.1 | 0.1 |
| Cellulase | 0.1 | 0.1 | 0.1 | 0.1 | 0.1 | 0.1 | 0.1 | 0.1 |
| Lipase | 0.3 | 0.3 | 0.3 | 0.3 | 0.3 | 0.3 | 0.3 | 0.3 |
| Other additives: | | | | | | | | |
| Sodium sulfite | 1 | 1 | 1 | 1 | 1 | 1 | 1 | 1 |
| Perfume | 0.2 | 0.2 | 0.2 | 0.2 | 0.2 | 0.2 | 0.2 | 0.2 |
| Fluorescent agent | 0.4 | 0.4 | 0.4 | 0.4 | 0.4 | 0.4 | 0.4 | 0.4 |
| PAa | 0.3 | 0.3 | 0.3 | 0.3 | 0.3 | 0.3 | 0.3 | 0.3 |
| PEG400 | 0.2 | 0.2 | 0.2 | 0.2 | 0.2 | 0.2 | 0.2 | 0.2 |
| Sodium sulfate | | | | Balance | | | | |
| Detergency (%) | 86 | 88 | 86 | 86 | 85 | 85 | 84 | 85 |

TABLE 11

TABLE 11-continued

| Sample No. | 9 | 10 | 11 | 12 | 13 | 14 | 15 | 16 |
|---|---|---|---|---|---|---|---|---|
| Composition (wt. %) | | | | | | | | |
| Anionic: | | | | | | | | |
| α-SF | 20 | 20 | 20 | 20 | 20 | 20 | 20 | 20 |
| AOS | 3 | 3 | 3 | 3 | 3 | 3 | 3 | 3 |
| LAS | 2 | 2 | 2 | 2 | 2 | 2 | 2 | 2 |
| Nonionic: | | | | | | | | |
| AE | 5 | 5 | 5 | 5 | 5 | 5 | 5 | 5 |
| NFE | 3 | 3 | 3 | 3 | 3 | 3 | 3 | 3 |
| AOE.PO | 2 | 2 | 2 | 2 | 2 | 2 | 2 | 2 |
| FEE | — | — | — | — | — | — | — | — |
| Builders: | | | | | | | | |
| ASDA | 15 | 25 | 5 | 10 | 10 | 10 | 10 | 10 |
| Potassium carbonate | 8 | 8 | 8 | 8 | 8 | 8 | 8 | 8 |
| Sodium carbonate | 22 | 22 | 27 | 22 | 22 | 22 | 22 | 22 |
| Enzymes: | | | | | | | | |
| Protease | 0.5 | 0.5 | 0.5 | 0.5 | 0.5 | 0.5 | 0.5 | 0.5 |
| Amylase | 0.1 | 0.1 | 0.1 | — | 0.5 | — | — | 0.1 |
| Cellulase | 0.1 | 0.1 | 0.1 | — | — | 0.5 | — | 0.1 |
| Lipase | 0.3 | 0.3 | 0.3 | — | — | — | 0.5 | 0.3 |
| Other additives: | | | | | | | | |
| Sodium sulfite | 1 | 1 | 1 | 1 | 1 | 1 | 1 | 1 |
| Perfume | 0.2 | 0.2 | 0.2 | 0.2 | 0.2 | 0.2 | 0.2 | 0.2 |
| Fluorescent agent | 0.4 | 0.4 | 0.4 | 0.4 | 0.4 | 0.4 | 0.4 | 0.4 |
| PAa | 0.3 | 0.3 | 0.3 | 0.3 | 0.3 | 0.3 | 0.3 | 0.3 |
| PEG400 | 0.2 | 0.2 | 0.2 | 0.2 | 0.2 | 0.2 | 0.2 | 0.2 |
| Sodium sulfate | | | | Balance | | | | |
| Detergency (%) | 88 | 86 | 90 | 88 | 88 | 88 | 87 | 88 |

TABLE 12

| Sample No. | 17 | 18 | 19 | 20 | 21 | 22 | 23 | 24 |
|---|---|---|---|---|---|---|---|---|
| Composition (wt. %) | | | | | | | | |
| Anionic: | | | | | | | | |
| α-SF | 20 | 20 | 20 | 20 | 20 | 20 | 20 | 20 |
| AOS | 3 | 3 | 5 | — | 3 | 3 | 3 | 3 |
| LAS | 2 | 2 | — | 5 | 2 | 2 | 2 | 2 |
| Nonionic: | | | | | | | | |
| AE | 5 | 5 | 5 | 5 | 5 | — | — | — |
| NFE | 3 | 3 | 3 | 3 | — | 5 | — | — |
| AOE.PO | 2 | 2 | 2 | 2 | — | — | 5 | — |
| FEE | — | — | — | — | — | — | — | 5 |
| Builders: | | | | | | | | |
| TUDA | 5 | 10 | 10 | 10 | 10 | 10 | 10 | 10 |
| Potassium carbonate | 8 | 8 | 8 | 8 | 8 | 8 | 8 | 8 |
| Sodium carbonate | 22 | 22 | 22 | 22 | 22 | 22 | 22 | 22 |
| Enzymes: | | | | | | | | |
| Protease | 0.5 | 0.5 | 0.5 | 0.5 | 0.5 | 0.5 | 0.5 | 0.5 |
| Amylase | 0.1 | 0.1 | 0.1 | 0.1 | 0.1 | 0.1 | 0.1 | 0.1 |
| Cellulase | 0.1 | 0.1 | 0.1 | 0.1 | 0.1 | 0.1 | 0.1 | 0.1 |
| Lipase | 0.3 | 0.3 | 0.3 | 0.3 | 0.3 | 0.3 | 0.3 | 0.3 |
| Other additives: | | | | | | | | |
| Sodium sulfite | 1 | 1 | 1 | 1 | 1 | 1 | 1 | 1 |
| Perfume | 0.2 | 0.2 | 0.2 | 0.2 | 0.2 | 0.2 | 0.2 | 0.2 |
| Fluorescent agent | 0.4 | 0.4 | 0.4 | 0.4 | 0.4 | 0.4 | 0.4 | 0.4 |
| PAa | 0.3 | 0.3 | 0.3 | 0.3 | 0.3 | 0.3 | 0.3 | 0.3 |
| PEG400 | 0.2 | 0.2 | 0.2 | 0.2 | 0.2 | 0.2 | 0.2 | 0.2 |
| Sodium sulfate | | | | Balance | | | | |
| Detergency (%) | 84 | 87 | 87 | 85 | 84 | 85 | 86 | 85 |

TABLE 13

| Sample No. | 25 | 26 | 27 | 28 | 29 | 30 | 31 | 32 |
|---|---|---|---|---|---|---|---|---|
| Composition (wt. %) | | | | | | | | |
| Anionic: | | | | | | | | |
| α-SF | 20 | 20 | 20 | 20 | 20 | 20 | 20 | 20 |
| AOS | 3 | 3 | 3 | 3 | 3 | 3 | 3 | 3 |
| LAS | 2 | 2 | 2 | 2 | 2 | 2 | 2 | 2 |
| Nonionic: | | | | | | | | |
| AE | 5 | 5 | 5 | 5 | 5 | 5 | 5 | 5 |
| NFE | 3 | 3 | 3 | 3 | 3 | 3 | 3 | 3 |
| AOE.PO | 2 | 2 | 2 | 2 | 2 | 2 | 2 | 2 |
| FEE | — | — | — | — | — | — | — | — |
| Builders: | | | | | | | | |
| TUDA | 15 | 25 | 5 | 10 | 10 | 10 | 10 | 10 |
| Potassium carbonate | 8 | 8 | 8 | 8 | 8 | 8 | 8 | 8 |
| Sodium carbonate | 22 | 22 | 27 | 22 | 22 | 22 | 22 | 22 |
| Enzymes: | | | | | | | | |
| Protease | 0.5 | 0.5 | 0.5 | 0.5 | 0.5 | 0.5 | 0.5 | 0.5 |
| Amylase | 0.1 | 0.1 | 0.1 | — | 0.5 | — | — | 0.1 |
| Cellulase | 0.1 | 0.1 | 0.1 | — | — | 0.5 | — | 0.1 |
| Lipase | 0.3 | 0.3 | 0.3 | — | — | — | 0.5 | 0.3 |
| Other additives: | | | | | | | | |
| Sodium sulfite | 1 | 1 | 1 | 1 | 1 | 1 | 1 | 1 |
| Perfume | 0.2 | 0.2 | 0.2 | 0.2 | 0.2 | 0.2 | 0.2 | 0.2 |
| Fluorescent agent | 0.4 | 0.4 | 0.4 | 0.4 | 0.4 | 0.4 | 0.4 | 0.4 |
| PAa | 0.3 | 0.3 | 0.3 | 0.3 | 0.3 | 0.3 | 0.3 | 0.3 |
| PEG400 | 0.2 | 0.2 | 0.2 | 0.2 | 0.2 | 0.2 | 0.2 | 0.2 |
| Sodium sulfate | | | | Balance | | | | |
| Detergency (%) | 90 | 88 | 87 | 90 | 89 | 87 | 86 | 89 |

TABLE 14

| Sample No. | 33 | 34 | 35 | 36 | 37 | 38 | 39 | 40 |
|---|---|---|---|---|---|---|---|---|
| Composition (wt. %) | | | | | | | | |
| Anionic: | | | | | | | | |
| α-SF | 20 | 20 | 20 | 20 | 20 | 20 | 20 | 20 |
| AOS | 3 | 3 | 5 | — | 3 | 3 | 3 | 3 |
| LAS | 2 | 2 | — | 5 | 2 | 2 | 2 | 2 |
| Nonionic: | | | | | | | | |
| AE | 5 | 5 | 5 | 5 | 5 | — | — | — |
| NFE | 3 | 3 | 3 | 3 | — | 5 | — | — |
| AOE.PO | 2 | 2 | 2 | 2 | — | — | 5 | — |
| FEE | — | — | — | — | — | — | — | 5 |
| Builders: | | | | | | | | |
| Silicate | 15 | 15 | 15 | 15 | 15 | 15 | 15 | 15 |
| ASDA | 5 | 10 | 10 | 10 | 10 | 10 | 10 | 10 |
| Potassium carbonate | 8 | 8 | 8 | 8 | 8 | 8 | 8 | 8 |
| Sodium carbonate | 22 | 22 | 22 | 22 | 22 | 22 | 22 | 22 |
| Enzymes: | | | | | | | | |
| Protease | 0.5 | 0.5 | 0.5 | 0.5 | 0.5 | 0.5 | 0.5 | 0.5 |
| Amylase | 0.1 | 0.1 | 0.1 | 0.1 | 0.1 | 0.1 | 0.1 | 0.1 |
| Cellulase | 0.1 | 0.1 | 0.1 | 0.1 | 0.1 | 0.1 | 0.1 | 0.1 |
| Lipase | 0.3 | 0.3 | 0.3 | 0.3 | 0.3 | 0.3 | 0.3 | 0.3 |
| Other additives: | | | | | | | | |
| Sodium sulfite | 1 | 1 | 1 | 1 | 1 | 1 | 1 | 1 |
| Perfume | 0.2 | 0.2 | 0.2 | 0.2 | 0.2 | 0.2 | 0.2 | 0.2 |
| Fluorescent agent | 0.4 | 0.4 | 0.4 | 0.4 | 0.4 | 0.4 | 0.4 | 0.4 |
| PAa | 0.3 | 0.3 | 0.3 | 0.3 | 0.3 | 0.3 | 0.3 | 0.3 |
| PEG400 | 0.2 | 0.2 | 0.2 | 0.2 | 0.2 | 0.2 | 0.2 | 0.2 |

TABLE 14-continued

| Sample No. | 33 | 34 | 35 | 36 | 37 | 38 | 39 | 40 |
|---|---|---|---|---|---|---|---|---|
| Sodium sulfate | | | | Balance | | | | |
| Detergency (%) | 85 | 87 | 87 | 88 | 86 | 84 | 85 | 85 |

TABLE 15

| Sample No. | 41 | 42 | 43 | 44 | 45 | 46 | 47 | 48 |
|---|---|---|---|---|---|---|---|---|
| Composition (wt. %) | | | | | | | | |
| Anionic: | | | | | | | | |
| α-SF | 20 | 20 | 20 | 20 | 20 | 20 | 20 | 20 |
| AOS | 3 | 3 | 3 | 3 | 3 | 3 | 3 | 3 |
| LAS | 2 | 2 | 2 | 2 | 2 | 2 | 2 | 2 |
| Nonionic: | | | | | | | | |
| AE | 5 | 5 | 5 | 5 | 5 | 5 | 5 | 5 |
| NFE | 3 | 3 | 3 | 3 | 3 | 3 | 3 | 3 |
| AOE.PO | 2 | 2 | 2 | 2 | 2 | 2 | — | 2 |
| FEE | — | — | — | — | — | — | — | — |
| Builders: | | | | | | | | |
| Silicate | — | — | 15 | 15 | 15 | 15 | 15 | 15 |
| ASDA | 15 | 25 | 5 | 10 | 10 | 10 | 10 | 10 |
| Potassium carbonate | 8 | 8 | 8 | 8 | 8 | 8 | 8 | 8 |
| Sodium carbonate | 22 | 22 | 27 | 22 | 22 | 22 | 22 | 22 |
| Enzymes: | | | | | | | | |
| Protease | 0.5 | 0.5 | 0.5 | 0.5 | 0.5 | 0.5 | 0.5 | 0.5 |
| Amylase | 0.1 | 0.1 | 0.1 | — | 0.5 | — | — | 0.1 |
| Cellulase | 0.1 | 0.1 | 0.1 | — | — | 0.5 | — | 0.1 |
| Lipase | 0.3 | 0.3 | 0.3 | — | — | — | 0.5 | 0.3 |
| Other additives: | | | | | | | | |
| Sodium sulfite | 1 | 1 | 1 | 1 | 1 | 1 | 1 | 1 |
| Perfume | 0.2 | 0.2 | 0.2 | 0.2 | 0.2 | 0.2 | 0.2 | 0.2 |
| Fluorescent agent | 0.4 | 0.4 | 0.4 | 0.4 | 0.4 | 0.4 | 0.4 | 0.4 |
| PAa | 0.3 | 0.3 | 0.3 | 0.3 | 0.3 | 0.3 | 0.3 | 0.3 |
| PEG400 | 0.2 | 0.2 | 0.2 | 0.2 | 0.2 | 0.2 | 0.2 | 0.2 |
| Sodium sulfate | | | | Balance | | | | |
| Detergency (%) | 86 | 87 | 90 | 87 | 88 | 86 | 88 | 87 |

TABLE 16

| Sample No. | 49 | 50 | 51 | 52 | 53 | 54 | 55 | 56 |
|---|---|---|---|---|---|---|---|---|
| Composition (wt. %) | | | | | | | | |
| Anionic: | | | | | | | | |
| α-SF | 20 | 20 | 20 | 20 | 20 | 20 | 20 | 20 |
| AOS | 3 | 3 | 5 | — | 3 | 3 | 3 | 3 |
| LAS | 2 | 2 | — | 5 | 2 | 2 | 2 | 2 |
| Nonionic: | | | | | | | | |
| AE | 5 | 5 | 5 | 5 | 5 | — | — | — |
| NFE | 3 | 3 | 3 | 3 | — | 5 | — | — |
| AOE.PO | 2 | 2 | 2 | 2 | — | — | 5 | — |
| FEE | — | — | — | — | — | — | — | 5 |
| Builders: | | | | | | | | |
| Silicate | 15 | 15 | 15 | 15 | 15 | 15 | 15 | 15 |
| TUDA | 5 | 10 | 10 | 10 | 10 | 10 | 10 | 10 |
| Potassium carbonate | 8 | 8 | 8 | 8 | 8 | 8 | 8 | 8 |
| Sodium carbonate | 22 | 22 | 27 | 22 | 22 | 22 | 22 | 22 |
| Enzymes: | | | | | | | | |
| Protease | 0.5 | 0.5 | 0.5 | 0.5 | 0.5 | 0.5 | 0.5 | 0.5 |
| Amylase | 0.1 | 0.1 | 0.1 | 0.1 | 0.1 | 0.1 | 0.1 | 0.1 |

TABLE 16-continued

| Sample No. | 49 | 50 | 51 | 52 | 53 | 54 | 55 | 56 |
|---|---|---|---|---|---|---|---|---|
| Cellulase | 0.1 | 0.1 | 0.1 | 0.1 | 0.1 | 0.1 | 0.1 | 0.1 |
| Lipase | 0.3 | 0.3 | 0.3 | 0.3 | 0.3 | 0.3 | 0.3 | 0.3 |
| Other additives: | | | | | | | | |
| Sodium sulfite | 1 | 1 | 1 | 1 | 1 | 1 | 1 | 1 |
| Perfume | 0.2 | 0.2 | 0.2 | 0.2 | 0.2 | 0.2 | 0.2 | 0.2 |
| Fluorescent agent | 0.4 | 0.4 | 0.4 | 0.4 | 0.4 | 0.4 | 0.4 | 0.4 |
| PAa | 0.3 | 0.3 | 0.3 | 0.3 | 0.3 | 0.3 | 0.3 | 0.3 |
| PEG400 | 0.2 | 0.2 | 0.2 | 0.2 | 0.2 | 0.2 | 0.2 | 0.2 |
| Sodium sulfate | | | | Balance | | | | |
| Detergency (%) | 87 | 88 | 87 | 85 | 86 | 86 | 85 | 84 |

TABLE 17

| Sample No. | 57 | 58 | 59 | 60 | 61 | 62 | 63 | 64 |
|---|---|---|---|---|---|---|---|---|
| Composition (wt. %) | | | | | | | | |
| Anionic: | | | | | | | | |
| α-SF | 20 | 20 | 20 | 20 | 20 | 20 | 20 | 20 |
| AOS | 3 | 3 | 3 | 3 | 3 | 3 | 3 | 3 |
| LAS | 2 | 2 | 2 | 2 | 2 | 2 | 2 | 2 |
| Nonionic: | | | | | | | | |
| AE | 5 | 5 | 5 | 5 | 5 | 5 | 5 | 5 |
| NFE | 3 | 3 | 3 | 3 | 3 | 3 | 3 | 3 |
| AOE.PO | 2 | 2 | 2 | 2 | 2 | 2 | 2 | 2 |
| FEE | — | — | — | — | — | — | — | — |
| Builders: | | | | | | | | |
| Silicate | — | — | 15 | 15 | 15 | 15 | 15 | 15 |
| TUDA | 15 | 25 | 5 | 10 | 10 | 10 | 10 | 10 |
| Potassium carbonate | 8 | 8 | 8 | 8 | 8 | 8 | 8 | 8 |
| Sodium carbonate | 22 | 22 | 27 | 22 | 22 | 22 | 22 | 22 |
| Enzymes: | | | | | | | | |
| Protease | 0.5 | 0.5 | 0.5 | 0.5 | 0.5 | 0.5 | 0.5 | 0.5 |
| Amylase | 0.1 | 0.1 | 0.1 | — | 0.5 | — | — | 0.1 |
| Cellulase | 0.1 | 0.1 | 0.1 | — | — | 0.5 | — | 0.1 |
| Lipase | 0.3 | 0.3 | 0.3 | — | — | — | 0.5 | 0.3 |
| Other additives: | | | | | | | | |
| Sodium sulfite | 1 | 1 | 1 | 1 | 1 | 1 | 1 | 1 |
| Perfume | 0.2 | 0.2 | 0.2 | 0.2 | 0.2 | 0.2 | 0.2 | 0.2 |
| Fluorescent agent | 0.4 | 0.4 | 0.4 | 0.4 | 0.4 | 0.4 | 0.4 | 0.4 |
| PAa | 0.3 | 0.3 | 0.3 | 0.3 | 0.3 | 0.3 | 0.3 | 0.3 |
| PEG400 | 0.2 | 0.2 | 0.2 | 0.2 | 0.2 | 0.2 | 0.2 | 0.2 |
| Sodium sulfate | | | | Balance | | | | |
| Detergency (%) | 90 | 87 | 88 | 87 | 88 | 87 | 89 | 86 |

TABLE 18

| Sample No. | 65 | 66 | 67 | 68 | 69 | 70 | 71 | 72 |
|---|---|---|---|---|---|---|---|---|
| Composition (wt. %) | | | | | | | | |
| Anionic: | | | | | | | | |
| α-SF | 20 | 20 | 20 | 20 | 20 | 20 | 20 | 20 |
| AOS | 3 | 3 | 5 | — | 3 | 3 | 3 | 3 |
| LAS | 2 | 2 | — | 5 | 2 | 2 | 2 | 2 |
| Nonionic: | | | | | | | | |
| AE | 5 | 5 | 5 | 5 | 5 | — | — | — |
| NFE | 3 | 3 | 3 | 3 | — | 5 | — | — |
| AOE.PO | 2 | 2 | 2 | 2 | — | — | 5 | — |
| FEE | — | — | — | — | — | — | — | 5 |

TABLE 18-continued

| Sample No. | 65 | 66 | 67 | 68 | 69 | 70 | 71 | 72 |
|---|---|---|---|---|---|---|---|---|
| Builders: | | | | | | | | |
| Silicate | 15 | 15 | 15 | 15 | 15 | 15 | 15 | 15 |
| ASDA | 5 | 10 | 10 | 10 | 10 | 10 | 10 | 10 |
| Potassium carbonate | 8 | 8 | 8 | 8 | 8 | 8 | 8 | 8 |
| Sodium carbonate | 22 | 22 | 22 | 22 | 22 | 22 | 22 | 22 |
| Bleaching agents: | | | | | | | | |
| Sodium percarbonate | 10 | 10 | 10 | 10 | 10 | 10 | 10 | 10 |
| Sodium perborate | 10 | 10 | 10 | 10 | 10 | 10 | 10 | 10 |
| Enzymes: | | | | | | | | |
| Protease | 0.5 | 0.5 | 0.5 | 0.5 | 0.5 | 0.5 | 0.5 | 0.5 |
| Amylase | 0.1 | 0.1 | 0.1 | 0.1 | 0.1 | 0.1 | 0.1 | 0.1 |
| Cellulase | 0.1 | 0.1 | 0.1 | 0.1 | 0.1 | 0.1 | 0.1 | 0.1 |
| Lipase | 0.3 | 0.3 | 0.3 | 0.3 | 0.3 | 0.3 | 0.3 | 0.3 |
| Other additives: | | | | | | | | |
| Sodium sulfite | 1 | 1 | 1 | 1 | 1 | 1 | 1 | 1 |
| Perfume | 0.2 | 0.2 | 0.2 | 0.2 | 0.2 | 0.2 | 0.2 | 0.2 |
| Fluorescent agent | 0.4 | 0.4 | 0.4 | 0.4 | 0.4 | 0.4 | 0.4 | 0.4 |
| PAa | 0.3 | 0.3 | 0.3 | 0.3 | 0.3 | 0.3 | 0.3 | 0.3 |
| PEG400 | 0.2 | 0.2 | 0.2 | 0.2 | 0.2 | 0.2 | 0.2 | 0.2 |
| Sodium sulfate | | | | Balance | | | | |
| Detergency (%) | 85 | 86 | 87 | 87 | 86 | 85 | 85 | 85 |

TABLE 19

| Sample No. | 73 | 74 | 75 | 76 | 77 | 78 | 79 | 80 |
|---|---|---|---|---|---|---|---|---|
| Composition (wt. %) | | | | | | | | |
| Anionic: | | | | | | | | |
| α-SF | 20 | 20 | 20 | 20 | 20 | 20 | 20 | 20 |
| AOS | 3 | 3 | 3 | 3 | 3 | 3 | 3 | 3 |
| LAS | 2 | 2 | 2 | 2 | 2 | 2 | 2 | 2 |
| Nonionic: | | | | | | | | |
| AE | 5 | 5 | 5 | 5 | 5 | 5 | 5 | 5 |
| NFE | 3 | 3 | 3 | 3 | 3 | 3 | 3 | 3 |
| AOE.PO | 2 | 2 | 2 | 2 | 2 | 2 | 2 | 2 |
| FEE | — | — | — | — | — | — | — | — |
| Builders: | | | | | | | | |
| Silicate | — | — | 15 | 15 | 15 | 15 | 15 | 15 |
| ASDA | 15 | 25 | 5 | 10 | 10 | 10 | 10 | 10 |
| Potassium carbonate | 8 | 8 | 8 | 8 | 8 | 8 | 8 | 8 |
| Sodium carbonate | 22 | 22 | 27 | 22 | 22 | 22 | 22 | 22 |
| Bleaching agents: | | | | | | | | |
| Sodium percarbonate | 10 | 10 | 10 | 10 | 10 | 10 | 10 | 10 |
| Sodium perborate | 10 | 10 | 10 | 10 | 10 | 10 | 10 | 10 |
| Enzymes: | | | | | | | | |
| Protease | 0.5 | 0.5 | 0.5 | 0.5 | 0.5 | 0.5 | 0.5 | 0.5 |
| Amylase | 0.1 | 0.1 | 0.1 | — | 0.5 | — | — | 0.1 |
| Cellulase | 0.1 | 0.1 | 0.1 | — | — | 0.5 | — | 0.1 |
| Lipase | 0.3 | 0.3 | 0.3 | — | — | — | 0.5 | 0.3 |
| Other additives: | | | | | | | | |
| Sodium sulfite | 1 | 1 | 1 | 1 | 1 | 1 | 1 | 1 |
| Perfume | 0.2 | 0.2 | 0.2 | 0.2 | 0.2 | 0.2 | 0.2 | 0.2 |
| Fluorescent agent | 0.4 | 0.4 | 0.4 | 0.4 | 0.4 | 0.4 | 0.4 | 0.4 |
| PAa | 0.3 | 0.3 | 0.3 | 0.3 | 0.3 | 0.3 | 0.3 | 0.3 |
| PEG400 | 0.2 | 0.2 | 0.2 | 0.2 | 0.2 | 0.2 | 0.2 | 0.2 |

TABLE 19-continued

| Sample No. | 73 | 74 | 75 | 76 | 77 | 78 | 79 | 80 |
|---|---|---|---|---|---|---|---|---|
| Sodium sulfate | | | | Balance | | | | |
| Detergency (%) | 90 | 88 | 87 | 86 | 87 | 88 | 88 | 87 |

TABLE 20

| Sample No. | 81 | 82 | 83 | 84 | 85 | 86 | 87 | 88 |
|---|---|---|---|---|---|---|---|---|
| Composition (wt. %) | | | | | | | | |
| Anionic: | | | | | | | | |
| α-SF | 20 | 20 | 20 | 20 | 20 | 20 | 20 | 20 |
| AOS | 3 | 3 | 5 | — | 3 | 3 | 3 | 3 |
| LAS | 2 | 2 | — | 5 | 2 | 2 | 2 | 2 |
| Nonionic: | | | | | | | | |
| AE | 5 | 5 | 5 | 5 | 5 | — | — | — |
| NFE | 3 | 3 | 3 | 3 | — | 5 | — | — |
| AOE.PO | 2 | 2 | 2 | 2 | — | — | 5 | — |
| FEE | — | — | — | — | — | — | — | 5 |
| Builders: | | | | | | | | |
| Silicate | 15 | 15 | 15 | 15 | 15 | 15 | 15 | 15 |
| TUDA | 5 | 10 | 10 | 10 | 10 | 10 | 10 | 10 |
| Potassium carbonate | 8 | 8 | 8 | 8 | 8 | 8 | 8 | 8 |
| Sodium carbonate | 22 | 22 | 22 | 22 | 22 | 22 | 22 | 22 |
| Bleaching agents: | | | | | | | | |
| Sodium percarbonate | 10 | 10 | 10 | 10 | 10 | 10 | 10 | 10 |
| Sodium perborate | 10 | 10 | 10 | 10 | 10 | 10 | 10 | 10 |
| Enzymes: | | | | | | | | |
| Protease | 0.5 | 0.5 | 0.5 | 0.5 | 0.5 | 0.5 | 0.5 | 0.5 |
| Amylase | 0.1 | 0.1 | 0.1 | 0.1 | 0.1 | 0.1 | 0.1 | 0.1 |
| Cellulase | 0.1 | 0.1 | 0.1 | 0.1 | 0.1 | 0.1 | 0.1 | 0.1 |
| Lipase | 0.3 | 0.3 | 0.3 | 0.3 | 0.3 | 0.3 | 0.3 | 0.3 |
| Other additives: | | | | | | | | |
| Sodium sulfite | 1 | 1 | 1 | 1 | 1 | 1 | 1 | 1 |
| Perfume | 0.2 | 0.2 | 0.2 | 0.2 | 0.2 | 0.2 | 0.2 | 0.2 |
| Fluorescent agent | 0.4 | 0.4 | 0.4 | 0.4 | 0.4 | 0.4 | 0.4 | 0.4 |
| PAa | 0.3 | 0.3 | 0.3 | 0.3 | 0.3 | 0.3 | 0.3 | 0.3 |
| PEG400 | 0.2 | 0.2 | 0.2 | 0.2 | 0.2 | 0.2 | 0.2 | 0.2 |
| Sodium sulfate | | | | Balance | | | | |
| Detergency (%) | 84 | 85 | 87 | 87 | 88 | 84 | 88 | 85 |

TABLE 21

| Sample No. | 89 | 90 | 91 | 92 | 93 | 94 | 95 | 96 |
|---|---|---|---|---|---|---|---|---|
| Composition (wt. %) | | | | | | | | |
| Anionic: | | | | | | | | |
| α-SF | 20 | 20 | 20 | 20 | 20 | 20 | 20 | 20 |
| AOS | 3 | 3 | 3 | 3 | 3 | 3 | 3 | 3 |
| LAS | 2 | 2 | 2 | 2 | 2 | 2 | 2 | 2 |
| Nonionic: | | | | | | | | |
| AE | 5 | 5 | 5 | 5 | 5 | 5 | 5 | 5 |
| NFE | 3 | 3 | 3 | 3 | 3 | 3 | 3 | 3 |
| AOE.PO | 2 | 2 | 2 | 2 | 2 | 2 | 2 | 2 |
| FEE | — | — | — | — | — | — | — | — |
| Builders: | | | | | | | | |
| Silicate | — | — | 15 | 15 | 15 | 15 | 15 | 15 |
| TUDA | 15 | 25 | 5 | 10 | 10 | 10 | 10 | 10 |
| Potassium carbonate | 8 | 8 | 8 | 8 | 8 | 8 | 8 | 8 |

TABLE 21-continued

| Sample No. | 89 | 90 | 91 | 92 | 93 | 94 | 95 | 96 |
|---|---|---|---|---|---|---|---|---|
| Sodium carbonate | 22 | 22 | 27 | 22 | 22 | 22 | 22 | 22 |
| Bleaching agents: | | | | | | | | |
| Sodium percarbonate | 10 | 10 | 10 | 10 | 10 | 10 | 10 | 10 |
| Sodium perborate | 10 | 10 | 10 | 10 | 10 | 10 | 10 | 10 |
| Enzymes: | | | | | | | | |
| Protease | 0.5 | 0.5 | 0.5 | 0.5 | 0.5 | 0.5 | 0.5 | 0.5 |
| Amylase | 0.1 | 0.1 | 0.1 | — | 0.5 | — | — | 0.1 |
| Cellulase | 0.1 | 0.1 | 0.1 | — | — | 0.5 | — | 0.1 |
| Lipase | 0.3 | 0.3 | 0.3 | — | — | — | 0.5 | 0.3 |
| Other additives: | | | | | | | | |
| Sodium sulfite | 1 | 1 | 1 | 1 | 1 | 1 | 1 | 1 |
| Perfume | 0.2 | 0.2 | 0.2 | 0.2 | 0.2 | 0.2 | 0.2 | 0.2 |
| Fluorescent agent | 0.4 | 0.4 | 0.4 | 0.4 | 0.4 | 0.4 | 0.4 | 0.4 |
| PAa | 0.3 | 0.3 | 0.3 | 0.3 | 0.3 | 0.3 | 0.3 | 0.3 |
| PEG400 | 0.2 | 0.2 | 0.2 | 0.2 | 0.2 | 0.2 | 0.2 | 0.2 |
| Sodium sulfate | | | | Balance | | | | |
| Detergency (%) | 89 | 88 | 88 | 89 | 87 | 87 | 86 | 90 |

EXAMPLES 130–153

(1) Table 22 shows examples of the detergent compositions of the present invention containing some of the builders of (S)-aspartic acid-N,N-diacetic acid (ASDA), taurine-N,N-diacetic acid (TUDA), methyliminodiacetic acid (MIDA), (S)-aspartic acid-N-monoacetic acid (ASMA) and (S)-aspartic acid-N-monopropionic acid (ASMP).

Table 22 further shows the compositions of comparative examples where each of ethylenediaminetetraacetic acid (EDTA), nitrilotriacetic acid (NTA), ASDA, TUDA, MIDA, ASMA and ASMP was used alone as the builder.

(2) Table 23 shows $Ca^{++}$ trapping power of the builders per weight in terms of acid at the respective pH in the above examples and comparative examples. The $Ca^{++}$ trapping power was determined by the titration conducted using 1% by weight of aqueous calcium acetate solution in the presence of 100 ppm of sodium dodecylbenzenesulfonate as an indicator.

(3) Detergency test was conducted on the builders having the composition of the above examples and comparative examples or zeolite and sodium tripolyphosphate (STPP). An artificially soiled cotton cloth, 1000 ml of tap water (hardness: 5° DH) of 25° C. and 1.2 g of the detergent composition were put in a cleaning apparatus (Terg-O-Tometer), followed by adjusting to a predetermined pH with 48% aqueous sodium hydroxide solution. Then, cleaning was carried out at a revolution number of 200 per minute for 10 minutes. Furthermore, after draining off, 1000 ml of tap water (hardness: 3° DH) of 25° C. was added freshly and rinsing 5 was carried out at 200 rpm for 5 minutes. The results are shown in Table 24.

The detergency was obtained by the following formula.

$$\text{Detergency (\%)} = \frac{\text{Reflectance of cloth after cleaned} - \text{Reflectance of cloth before cleaned}}{\text{Reflectance of unsoiled chloth} - \text{Reflectance of cloth before cleaned}} \times 100$$

The detergent composition used had the following composition. As the surface active agent, sodium dodecylbenzenesulfonate (SDS) or sodium laurate (SLA) was selected.

| | |
|---|---|
| Surface active agent | 25 wt % |
| Builder | 25 wt % (in terms of acid) |
| Sodium silicate | 5 wt % |
| Sodium carbonate | 3 wt % |
| Carboxymethylcellulose | 1 wt % |
| Sodium sulfate | 41 wt % |

TABLE 22

| | Composition of builder | | | | |
|---|---|---|---|---|---|
| Example | ASDA | TUDA | MIDA | ASMA | ASMP |
| Example 130 | 60 | 20 | 20 | 0 | 0 |
| Example 131 | 60 | 10 | 30 | 0 | 0 |
| Example 132 | 50 | 25 | 25 | 0 | 0 |
| Example 133 | 50 | 10 | 40 | 0 | 0 |
| Example 134 | 50 | 40 | 20 | 0 | 0 |
| Example 135 | 40 | 30 | 30 | 0 | 0 |
| Example 136 | 40 | 40 | 10 | 0 | 0 |
| Example 137 | 40 | 10 | 40 | 0 | 0 |
| Example 138 | 30 | 35 | 35 | 0 | 0 |
| Example 139 | 30 | 60 | 10 | 0 | 0 |
| Example 140 | 20 | 10 | 60 | 0 | 0 |
| Example 141 | 20 | 10 | 40 | 10 | 0 |
| Example 142 | 90 | 10 | 0 | 0 | 0 |
| Example 143 | 50 | 50 | 0 | 0 | 0 |
| Example 144 | 20 | 80 | 0 | 0 | 0 |
| Example 145 | 80 | 20 | 0 | 0 | 0 |
| Example 146 | 20 | 10 | 40 | 10 | 0 |
| Example 147 | 90 | 10 | 0 | 0 | 0 |
| Example 148 | 95 | 0 | 5 | 0 | 0 |
| Example 149 | 80 | 5 | 15 | 0 | 0 |
| Example 150 | 80 | 15 | 5 | 0 | 0 |
| Example 151 | 10 | 0 | 0 | 80 | 10 |
| Example 152 | 20 | 0 | 0 | 80 | 0 |
| Example 153 | 45 | 0 | 0 | 50 | 5 |

TABLE 23

| Composition of | | $Ca^{++}$ trapping power [$CaCO_3$ mg/builder (g) in terms of acid] | | | | | | | |
|---|---|---|---|---|---|---|---|---|---|
| builder | pH | 7.0 | 8.0 | 8.5 | 9.0 | 10.0 | 11.0 | 12.0 | 13.0 |
| Example 130 | | 214 | 271 | 316 | 340 | 460 | 536 | 621 | 624 |
| Example 131 | | 206 | 208 | 276 | 305 | 474 | 569 | 659 | 668 |
| Example 132 | | 188 | 255 | 307 | 336 | 477 | 558 | 633 | 637 |
| Example 133 | | 176 | 209 | 248 | 284 | 499 | 606 | 691 | 708 |
| Example 134 | | 199 | 304 | 374 | 403 | 519 | 592 | 665 | 671 |
| Example 135 | | 162 | 239 | 299 | 332 | 495 | 579 | 646 | 650 |
| Example 136 | | 169 | 268 | 332 | 353 | 416 | 464 | 519 | 518 |
| Example 137 | | 144 | 175 | 213 | 248 | 460 | 561 | 634 | 648 |
| Example 138 | | 137 | 223 | 290 | 328 | 512 | 601 | 658 | 663 |
| Example 139 | | 157 | 300 | 390 | 415 | 475 | 520 | 562 | 565 |
| Example 140 | | 86 | 145 | 203 | 254 | 559 | 687 | 747 | 761 |
| Example 141 | | 81 | 152 | 210 | 262 | 482 | 640 | 697 | 708 |
| Example 142 | | 294 | 335 | 361 | 370 | 400 | 456 | 564 | 569 |
| Example 143 | | 208 | 333 | 407 | 423 | 440 | 477 | 538 | 541 |
| Example 144 | | 71 | 331 | 441 | 464 | 471 | 493 | 517 | 518 |
| Example 145 | | 273 | 335 | 372 | 383 | 410 | 461 | 558 | 566 |
| Example 146 | | 83 | 114 | 153 | 195 | 408 | 530 | 580 | 598 |
| Example 147 | | 305 | 337 | 355 | 345 | 402 | 469 | 587 | 593 |
| Example 148 | | 301 | 320 | 335 | 345 | 402 | 469 | 587 | 593 |
| Example 149 | | 261 | 288 | 313 | 331 | 432 | 469 | 587 | 593 |
| Example 150 | | 269 | 319 | 352 | 366 | 417 | 477 | 577 | 579 |
| Example 151 | | 51 | 80 | 120 | 187 | 263 | 555 | 578 | 587 |
| Example 152 | | 79 | 110 | 151 | 216 | 282 | 563 | 598 | 616 |
| Example 153 | | 154 | 180 | 210 | 254 | 313 | 517 | 578 | 582 |

TABLE 24

| Composition of builder | Surface active agent | pH | Detergency [%] |
|---|---|---|---|
| Example 130 | SDS | 8 | 56.6 |
| Example 131 | SDS | 11 | 59.5 |
| Example 132 | SDS | 9 | 58.0 |
| Example 133 | SDS | 12 | 60.1 |
| Example 134 | SLA | 12 | 51.3 |
| Example 135 | SDS | 8 | 55.4 |
| Example 136 | SDS | 8 | 61.1 |
| Example 137 | SDS | 10 | 58.2 |
| Example 138 | SLA | 10 | 51.1 |
| Example 139 | SDS | 9 | 56.6 |
| Example 140 | SDS | 11 | 61.3 |
| Example 141 | SDS | 10 | 60.0 |
| Example 142 | SLA | 9 | 50.2 |
| Example 143 | SDS | 8 | 57.7 |
| Example 144 | SDS | 9 | 58.9 |
| Example 145 | SDS | 7 | 58.1 |
| Example 146 | SDS | 12 | 60.0 |
| Example 147 | SLA | 11 | 53.2 |
| Example 148 | SLA | 12 | 51.6 |
| Example 149 | SLA | 13 | 54.8 |
| Example 150 | SDS | 9 | 57.4 |
| Example 151 | SDS | 12 | 60.1 |
| Example 152 | SDS | 12 | 60.2 |
| Example 153 | SDS | 12 | 60.3 |
| Zeolite | SDS | 12 | 48.1 |
| STPP | SDS | 12 | 60.5 |

As can be seen from Tables 23 and 24, the detergent compositions of the present invention exhibit, in a wide pH range, the $Ca^{++}$ trapping power and detergency far superior to those of the compositions which contained aspartic acid-N,N-diacetic acid, taurine-N,N-diacetic acid, methyliminodiacetic acid, aspartic acid-N-monoacetic acid, aspartic acid-N-monopropionic acid, nitrilotriacetic acid or zeolite each alone as a single builder, and, further, they exhibit excellent detergency equal to or higher than that of sodium tripolyphosphate or ethylenediaminetetraacetic acid. The detergent compositions of the present invention contain safe biodegradable builders substitutable for the conventional builders such as sodium tripolyphosphate, ethylenediaminetetraacetic acid and nitrilotriacetic acid which have the problems of eutrophication, non-biodegradation and toxicity.

EXAMPLE 154

The detergent compositions shown in Tables 25, 26 and 27 were prepared and evaluated on the detergency.

The abbreviations of the components are shown below.

S-ASDA: Tetrasodium salt of (S)-aspartic acid-N,N-diacetic acid

S-GLDA: Tetrasodium salt of (S)-glutamic acid-N,N-diacetic acid

TUDA: Trisodium salt of taurine-N,N-diacetic acid

SLA: Sodium laurate

SMA: Sodium myristate

CMC: Carboxymethylcellulose

TABLE 25

| Sample No. | 1 | 2 | 3 | 4 | 5 | 6 | 7 | 8 | 9 | 10 |
|---|---|---|---|---|---|---|---|---|---|---|
| Composition (wt. %) | | | | | | | | | | |
| S-ASDA | 25 | 25 | 25 | 25 | 25 | 0 | 0 | 0 | 0 | 0 |
| S-GLDA | 0 | 0 | 0 | 0 | 0 | 25 | 25 | 25 | 25 | 25 |
| TUDA | 0 | 0 | 0 | 0 | 0 | 0 | 0 | 0 | 0 | 0 |

TABLE 25-continued

| Sample No. | 1 | 2 | 3 | 4 | 5 | 6 | 7 | 8 | 9 | 10 |
|---|---|---|---|---|---|---|---|---|---|---|
| SLA | 25 | 0 | 20 | 15 | 10 | 25 | 0 | 20 | 15 | 10 |
| SMA | 0 | 25 | 5 | 10 | 15 | 0 | 25 | 5 | 10 | 15 |
| Sodium silicate | 5 | 5 | 5 | 5 | 5 | 5 | 5 | 5 | 5 | 5 |
| Potassium carbonate | 3 | 3 | 3 | 3 | 3 | 3 | 3 | 3 | 3 | 3 |
| CMC | 1 | 1 | 1 | 1 | 1 | 1 | 1 | 1 | 1 | 1 |
| Sodium sulfate | 41 | 41 | 41 | 41 | 41 | 41 | 41 | 41 | 41 | 41 |
| Detergency (%) | 90 | 88 | 88 | 86 | 85 | 85 | 84 | 85 | 84 | 87 |

TABLE 26

| Sample No. | 11 | 12 | 13 | 14 | 15 | 16 | 17 | 18 | 19 | 20 |
|---|---|---|---|---|---|---|---|---|---|---|
| Composition (wt. %) | | | | | | | | | | |
| S-ASDA | 0 | 0 | 0 | 0 | 0 | 15 | 15 | 15 | 15 | 15 |
| S-GLDA | 0 | 0 | 0 | 0 | 0 | 10 | 10 | 10 | 10 | 10 |
| TUDA | 25 | 25 | 25 | 25 | 25 | 0 | 0 | 0 | 0 | 0 |
| SLA | 25 | 0 | 20 | 15 | 10 | 25 | 0 | 20 | 15 | 10 |
| SMA | 0 | 25 | 5 | 10 | 15 | 0 | 25 | 5 | 10 | 15 |
| Sodium silicate | 5 | 5 | 5 | 5 | 5 | 5 | 5 | 5 | 5 | 5 |
| Potassium carbonate | 3 | 3 | 3 | 3 | 3 | 3 | 3 | 3 | 3 | 3 |
| CMC | 1 | 1 | 1 | 1 | 1 | 1 | 1 | 1 | 1 | 1 |
| Sodium sulfate | 41 | 41 | 41 | 41 | 41 | 41 | 41 | 41 | 41 | 41 |
| Detergency (%) | 85 | 88 | 85 | 87 | 88 | 88 | 85 | 86 | 85 | 86 |

TABLE 27

| Sample No. | 21 | 22 | 23 | 24 | 25 | 26 | 27 | 28 | 29 | 30 |
|---|---|---|---|---|---|---|---|---|---|---|
| Composition (wt. %) | | | | | | | | | | |
| S-ASDA | 15 | 15 | 15 | 15 | 15 | 10 | 10 | 10 | 10 | 10 |
| S-GLDA | 0 | 0 | 0 | 0 | 0 | 10 | 5 | 10 | 5 | 10 |
| TUDA | 10 | 10 | 10 | 10 | 10 | 5 | 10 | 5 | 10 | 5 |
| SLA | 25 | 0 | 20 | 15 | 10 | 25 | 0 | 20 | 15 | 10 |
| SMA | 0 | 25 | 5 | 10 | 15 | 0 | 25 | 5 | 10 | 15 |
| Sodium silicate | 5 | 5 | 5 | 5 | 5 | 5 | 5 | 5 | 5 | 5 |
| Potassium carbonate | 3 | 3 | 3 | 3 | 3 | 3 | 3 | 3 | 3 | 3 |
| CMC | 1 | 1 | 1 | 1 | 1 | 1 | 1 | 1 | 1 | 1 |
| Sodium sulfate | 41 | 41 | 41 | 41 | 41 | 41 | 4i | 41 | 41 | 41 |
| Detergency (%) | 88 | 87 | 87 | 86 | 85 | 84 | 87 | 88 | 88 | 86 |

Biodegradability Test

The biodegradability of iminodiacetic acid derivatives used in the present invention was tested by the amended SCAS method which is a method for the biodegradability test using activated sludge described in the OECD chemical product testing guideline.

Test Method (1) 150 ml of an activated sludge mixed solution was charged in a test tank and exposed to air by an air pump.

(2) The exposure to air was continued for 23 hours and, then, stopped, and the sludge was settled for 45 minutes, followed by removing 100 ml of the supernatant liquid.

(3) 95 ml of the waste water left to stand and a test substance undiluted solution (400 mg/l) were charged in the test tank and 100 ml of waste water left to stand was charged in a tank for the control sample, and the content of the tanks was again exposed to air.

(4) The above procedure was repeated every day and the supernatant liquid was sampled, and retention rate of the test substance was traced by HPLC (high percision liquid chromatography) method and TOC (dissolved organic carbon) method.

Results

Tetrasodium salt of (S)-aspartic acid-N,N-diacetic acid, racemic aspartic acid-N,N-diacetatic acid tetrasodium salt, tetrasodium (S)-glutamic acid-N,N-diacetatic acid, racemic glutamic acid-N,N-diacetatic acid tetrasodium salt, trisodium salt of taurine-N,N-diacetic acid and tetrasodium ethylenediaminetetraacetate were tested in parallel. The retention rate obtained in each of the test methods is shown in Table 28.

TABLE 28

| Compound | Retention rate by HPLC (%) | Retention rate by TOC (%) |
|---|---|---|
| Tetrasodium salt of (S)-aspartic acid-N,N-diacetic acid | 0 | 0 |
| Racemic aspartic acid-N,N-diacetic acid tetrasodium salt | 65 | 50 |
| Tetrasodium salt of (S)-glutamic acid-N,N-diacetic acid | 0 | 0 |
| Racemic glutamic acid-N,N-diacetic acid tetrasodium salt | 60 | 50 |
| Trisodium salt of taurine-N,N-diacetic acid | 0 | 0 |
| Tetrasodium ethylenediaminetetra-acetate | 100 | 100 |

What is claimed is:

1. A chelating agent which comprises (i) at least one compound selected from the group consisting of α-alanine-N,N-diacetic acid and alkali metal salts and ammonia salts thereof and (ii) at least one compound selected from the group consisting of aspartic acid, maleic acid, acrylic acid, malic acid, glycine, glycolic acid, iminodiacetic acid, nitrilotriacetic acid, iminodipropionic acid, fumaric acid, a synthetic starting amino acid, a synthetic intermediate amino acid and a salt thereof in an amount of 0.3% or more by weight but 8% by weight or less based on the compound of (i).

2. A chelating agent in the form of aqueous solution or slurry which comprises (i) at least one compound selected from the group consisting of α-alanine-N,N-diacetic acid and alkali metal salts and ammonia salts thereof and (ii) at least one compound selected from the group consisting of aspartic acid, maleic acid, acrylic acid, malic acid, glycine, glycolic acid, iminodiacetic acid, nitrilotriacetic acid, iminodipropionic acid, fumaric acid, a synthetic starting amino acid, a synthetic intermediate amino acid and a salt thereof in an amount of 0.3% or more by weight but 25% by weight or less in total based on the compound of (i).

3. The chelating agent according to claim 1 or 2, wherein the α-alanine-N,N-diacetic acid is (S)-α-alanine-N,N-diacetic acid.

4. The chelating agent according to claim 1, wherein the compound (ii) further includes at least one compound selected from the group consisting of α-alanine and β-alanine.

5. The chelating agent according to claim 2, wherein the compound (ii) further includes at least one compound selected from the group consisting of α-alanine and β-alanine.

* * * * *